(12) United States Patent
Shachar et al.

(10) Patent No.: US 8,457,714 B2
(45) Date of Patent: Jun. 4, 2013

(54) SYSTEM AND METHOD FOR A CATHETER IMPEDANCE SEEKING DEVICE

(75) Inventors: Yehoshua Shachar, Santa Monica, CA (US); Bruce Marx, Ojai, CA (US); Leslie Farkas, Ojai, CA (US); Laszlo Farkas, Ojai, CA (US); David Johnson, West Hollywood, CA (US); Eli Gang, Los Angeles, CA (US)

(73) Assignee: Magnetecs, Inc., Inglewood, CA (US)

( * ) Notice: Subject to any disclaimer, the term of this patent is extended or adjusted under 35 U.S.C. 154(b) by 1060 days.

(21) Appl. No.: 12/323,231

(22) Filed: Nov. 25, 2008

(65) Prior Publication Data

US 2010/0130854 A1  May 27, 2010

(51) Int. Cl.
*A61B 5/05* (2006.01)
*A61B 17/00* (2006.01)

(52) U.S. Cl.
USPC .......................................................... 600/424

(58) Field of Classification Search
USPC .... 600/433–435, 585, 424; 604/95.01–95.05, 604/528, 529; 606/108; 128/897–898
See application file for complete search history.

(56) References Cited

U.S. PATENT DOCUMENTS

| | | | |
|---|---|---|---|
| 3,043,309 A | 9/1959 | McCarthy | |
| 3,358,676 A | 12/1967 | Frei et al. | |
| 3,622,869 A | 11/1971 | Golay | |
| 3,628,527 A | 12/1971 | West | |
| 3,746,937 A | 7/1973 | Koike | |
| 3,961,632 A | 6/1976 | Moossun | |
| 4,063,561 A | 12/1977 | McKenna | |
| 4,096,862 A | 6/1978 | DeLuca | |
| 4,162,679 A | 7/1979 | Reenstierna | |
| 4,173,228 A | 11/1979 | Van Steenwyk et al. | |
| 4,244,362 A | 1/1981 | Anderson | |
| 4,249,536 A | 2/1981 | Vega | |
| 4,270,252 A | 6/1981 | Harrison et al. | |
| 4,292,961 A | 10/1981 | Kawashima | |
| 4,354,501 A | 10/1982 | Colley et al. | |
| 4,392,634 A | 7/1983 | Kita | |
| 4,671,287 A | 6/1987 | Fiddian-Green | |
| 4,727,344 A | 2/1988 | Koga et al. | |
| 4,735,211 A | 4/1988 | Takasugi | |
| 4,809,713 A | 3/1989 | Grayzel | |

(Continued)

FOREIGN PATENT DOCUMENTS

DE  102005045073 A1  3/2007
EP  0147082 A2  7/1985

(Continued)

OTHER PUBLICATIONS

Office Action dated Aug. 25, 2009 from Related U.S. Appl. No. 10/621,196.

(Continued)

*Primary Examiner* — John Lacyk
(74) *Attorney, Agent, or Firm* — Knobbe, Martens, Olson & Bear, LLP

(57) ABSTRACT

A tissue-contact seeking method and apparatus is described that enhances catheter position detection and control systems in making and maintaining continuous tissue contact in a highly dynamic frame, such as under the rigors of cardiac motion. Tissue-seeking logical routines use a tissue contact sensing system to advance a catheter to relatively continuous tissue contact, or detect obstacles, in cooperation with the catheter position detection and control systems. Additional logical routines are capable of optimizing the contact direction of the catheter tip by controlling the rotation angle and chamber position of the introducer.

24 Claims, 23 Drawing Sheets

U.S. PATENT DOCUMENTS

| | | |
|---|---|---|
| 4,869,247 A | 9/1989 | Howard, III et al. |
| 4,870,306 A | 9/1989 | Petersen |
| 4,943,770 A | 7/1990 | Ashley-Rollman et al. |
| 4,984,581 A | 1/1991 | Stice |
| 4,985,015 A | 1/1991 | Obermann et al. |
| 5,063,935 A | 11/1991 | Gambale |
| 5,083,562 A | 1/1992 | de Coriolis et al. |
| 5,090,956 A | 2/1992 | McCoy |
| 5,125,888 A | 6/1992 | Howard et al. |
| 5,167,626 A | 12/1992 | Casper et al. |
| 5,209,234 A | 5/1993 | LaRocca |
| 5,226,847 A | 7/1993 | Thomas et al. |
| 5,249,163 A | 9/1993 | Erickson |
| 5,255,680 A | 10/1993 | Darrow et al. |
| 5,257,636 A | 11/1993 | White |
| 5,269,759 A | 12/1993 | Hernandez et al. |
| 5,353,807 A | 10/1994 | DeMarco |
| 5,377,678 A | 1/1995 | Dumoulin et al. |
| 5,396,902 A | 3/1995 | Brennen et al. |
| 5,462,054 A | 10/1995 | Rapoport et al. |
| 5,492,131 A | 2/1996 | Galel |
| 5,546,948 A | 8/1996 | Hamm et al. |
| 5,550,469 A | 8/1996 | Tanabe et al. |
| 5,558,091 A | 9/1996 | Acker et al. |
| 5,573,012 A | 11/1996 | McEwan |
| 5,588,442 A | 12/1996 | Scovil et al. |
| 5,624,430 A | 4/1997 | Eton et al. |
| 5,645,065 A | 7/1997 | Shapiro et al. |
| 5,650,725 A | 7/1997 | Powell et al. |
| 5,654,864 A | 8/1997 | Ritter et al. |
| 5,656,030 A | 8/1997 | Hunjan et al. |
| 5,681,260 A | 10/1997 | Ueda et al. |
| 5,683,384 A | 11/1997 | Gough et al. |
| 5,702,433 A | 12/1997 | Taylor et al. |
| 5,704,897 A | 1/1998 | Truppe |
| 5,709,661 A | 1/1998 | Van Egmond et al. |
| 5,711,299 A | 1/1998 | Manwaring et al. |
| 5,769,843 A | 6/1998 | Abela et al. |
| 5,775,322 A | 7/1998 | Silverstein et al. |
| 5,779,694 A | 7/1998 | Howard et al. |
| 5,808,665 A | 9/1998 | Green |
| 5,821,920 A | 10/1998 | Rosenberg et al. |
| 5,843,153 A | 12/1998 | Johnston et al. |
| 5,844,140 A | 12/1998 | Seale |
| 5,851,185 A | 12/1998 | Berns |
| 5,904,691 A | 5/1999 | Barnett et al. |
| 5,919,135 A | 7/1999 | Lemuelson |
| 5,931,818 A | 8/1999 | Werp et al. |
| 5,971,976 A | 10/1999 | Wang et al. |
| 6,014,580 A | 1/2000 | Blume et al. |
| 6,015,414 A | 1/2000 | Werp et al. |
| 6,038,488 A | 3/2000 | Barnes et al. |
| 6,104,944 A | 8/2000 | Martinelli |
| 6,122,538 A | 9/2000 | Sliwa et al. |
| 6,128,174 A | 10/2000 | Ritter et al. |
| 6,129,668 A | 10/2000 | Haynor et al. |
| 6,148,823 A | 11/2000 | Hastings |
| 6,152,933 A | 11/2000 | Werp et al. |
| 6,157,853 A | 12/2000 | Blume et al. |
| 6,200,312 B1 | 3/2001 | Zikorus et al. |
| 6,215,027 B1 | 4/2001 | Papavassiliou et al. |
| 6,241,671 B1 | 6/2001 | Ritter et al. |
| 6,292,678 B1 | 9/2001 | Hall et al. |
| 6,295,466 B1 | 9/2001 | Ishikawa et al. |
| 6,296,604 B1 | 10/2001 | Garibaldi et al. |
| 6,298,257 B1 | 10/2001 | Hall et al. |
| 6,304,768 B1 | 10/2001 | Blume et al. |
| 6,311,082 B1 | 10/2001 | Creighton, IV et al. |
| 6,314,312 B1 | 11/2001 | Wessels et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,381,485 B1 | 4/2002 | Hunter et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,454,776 B1 | 9/2002 | Tajima et al. |
| 6,459,924 B1 | 10/2002 | Creighton, IV et al. |
| 6,459,926 B1 | 10/2002 | Nowlin et al. |
| 6,475,223 B1 | 11/2002 | Werp et al. |
| 6,490,474 B1 | 12/2002 | Willis et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,529,761 B2 | 3/2003 | Creighton, IV et al. |
| 6,537,196 B1 | 3/2003 | Creighton, IV et al. |
| 6,562,019 B1 | 5/2003 | Sell |
| 6,575,977 B1 | 6/2003 | Michelson |
| 6,587,709 B2 | 7/2003 | Solf et al. |
| 6,594,517 B1 | 7/2003 | Nevo |
| 6,630,879 B1 | 10/2003 | Creighton, IV et al. |
| 6,662,034 B2 | 12/2003 | Segner et al. |
| 6,667,660 B2 | 12/2003 | Schrodinger et al. |
| 6,669,693 B2 | 12/2003 | Friedman |
| 6,677,752 B1 | 1/2004 | Creighton, IV et al. |
| 6,702,804 B1 | 3/2004 | Ritter et al. |
| 6,704,694 B1 | 3/2004 | Basdogan et al. |
| 6,726,675 B1 | 4/2004 | Beyar |
| 6,733,511 B2 | 5/2004 | Hall et al. |
| 6,740,103 B2 | 5/2004 | Hall et al. |
| 6,755,816 B2 | 6/2004 | Ritter et al. |
| 6,776,165 B2 | 8/2004 | Jin |
| 6,786,219 B2 | 9/2004 | Garibaldi et al. |
| 6,817,364 B2 | 11/2004 | Garibaldi et al. |
| 6,834,201 B2 | 12/2004 | Gillies et al. |
| 6,853,965 B2 | 2/2005 | Massie et al. |
| 6,902,528 B1 | 6/2005 | Garibaldi et al. |
| 6,914,552 B1 | 7/2005 | McEwan |
| 6,950,689 B1 | 9/2005 | Willis et al. |
| 6,960,847 B2 | 11/2005 | Suzuki et al. |
| 6,970,733 B2 | 11/2005 | Willis et al. |
| 7,280,863 B2 | 10/2007 | Shachar |
| 7,316,700 B2 | 1/2008 | Alden et al. |
| 7,341,063 B2 | 3/2008 | Garibaldi et al. |
| 7,346,379 B2 | 3/2008 | Eng et al. |
| 7,495,537 B2 | 2/2009 | Tunay |
| 7,543,239 B2 | 6/2009 | Viswanathan et al. |
| 7,725,157 B2 | 5/2010 | Dumoulin et al. |
| 2001/0004215 A1 | 6/2001 | Kubota et al. |
| 2001/0021805 A1 | 9/2001 | Blume et al. |
| 2002/0022777 A1 | 2/2002 | Creighton, IV et al. |
| 2002/0055674 A1 | 5/2002 | Ben-Haim et al. |
| 2002/0058866 A1 | 5/2002 | Segner et al. |
| 2002/0103430 A1 | 8/2002 | Hastings et al. |
| 2002/0168618 A1 | 11/2002 | Anderson et al. |
| 2003/0036696 A1 | 2/2003 | Willis et al. |
| 2003/0114727 A1 | 6/2003 | Wallace |
| 2003/0205941 A1 | 11/2003 | Suzuki et al. |
| 2003/0233112 A1 | 12/2003 | Alden et al. |
| 2004/0019447 A1 | 1/2004 | Shachar |
| 2004/0097805 A1 | 5/2004 | Verard et al. |
| 2004/0097806 A1 | 5/2004 | Hunter et al. |
| 2005/0004449 A1 | 1/2005 | Mitschke et al. |
| 2005/0021078 A1 | 1/2005 | Vleugels et al. |
| 2005/0096589 A1 | 5/2005 | Shachar |
| 2005/0203375 A1 | 9/2005 | Willis et al. |
| 2005/0256521 A1 | 11/2005 | Kozel |
| 2006/0058663 A1 | 3/2006 | Willis et al. |
| 2006/0114088 A1 | 6/2006 | Shachar |
| 2006/0116633 A1 | 6/2006 | Shachar |
| 2006/0116634 A1 | 6/2006 | Shachar |
| 2006/0217697 A1 | 9/2006 | Lau et al. |
| 2007/0016006 A1 | 1/2007 | Shachar |
| 2007/0062547 A1 | 3/2007 | Pappone |
| 2007/0066880 A1 | 3/2007 | Lee et al. |
| 2007/0197891 A1 | 8/2007 | Shachar |
| 2008/0027313 A1 | 1/2008 | Shachar |
| 2008/0039880 A1 | 2/2008 | Nohilly et al. |
| 2008/0058656 A1 | 3/2008 | Costello et al. |
| 2008/0091193 A1 | 4/2008 | Kauphusman et al. |
| 2008/0249395 A1 | 10/2008 | Shachar et al. |
| 2008/0297287 A1 | 12/2008 | Shachar et al. |
| 2009/0030411 A1 | 1/2009 | Werneth et al. |
| 2009/0209950 A1 | 8/2009 | Starksen |

| | | | |
|---|---|---|---|
| 2009/0248014 | A1 | 10/2009 | Shachar et al. |
| 2009/0253985 | A1 | 10/2009 | Shachar et al. |
| 2009/0275828 | A1 | 11/2009 | Shachar et al. |

FOREIGN PATENT DOCUMENTS

| | | |
|---|---|---|
| EP | 1059067 A1 | 12/2000 |
| EP | 1 115 327 | 7/2001 |
| GB | 2367803 A | 4/2002 |
| JP | 2000-509316 | 7/2000 |
| JP | 2001-448 | 1/2001 |
| JP | 2001-509038 | 7/2001 |
| JP | 2001-514040 | 9/2001 |
| WO | WO 95-01757 A1 | 1/1995 |
| WO | WO 97-29803 A1 | 8/1997 |
| WO | WO 98-35720 A2 | 8/1998 |
| WO | WO 99-11189 A1 | 3/1999 |
| WO | WO 99-23934 A2 | 5/1999 |
| WO | WO 00-76141 A1 | 2/2000 |
| WO | WO 02-19908 A1 | 3/2002 |
| WO | WO 02-34131 A1 | 5/2002 |
| WO | WO 02-094115 A2 | 11/2002 |
| WO | WO 02-094115 A3 | 11/2002 |
| WO | WO 2004-006795 A1 | 1/2004 |
| WO | WO 2005-042053 A2 | 5/2005 |
| WO | WO 2005-042053 A3 | 5/2005 |
| WO | WO 2005-112813 A1 | 12/2005 |
| WO | WO 2007-100559 A2 | 9/2007 |

OTHER PUBLICATIONS

Office Action dated Jul. 13, 2009 from Related U.S. Appl. No. 11/362,542.
International Search Report from PCT/US2007/004416, Aug. 24, 2007, 5 pages.
International Search Report from PCT/US2008/060525, Oct. 31, 2008, 6 pages.
International Search Report from PCT/US2008/056277, Nov. 18, 2008, 7 pages.
Supplementary Partial European Search Report from 04795885.5, Nov. 18, 2008, 5 pages.
Bergveld, Piet, "Development, Operation, and Application of the Ion-Sensitive Field-Effect Transistor as a Tool for Electrophysiology", IEEE Transactions on Biomedical Engineering, vol. BME-19, No. 5, Sep. 1972, 10 pages.
Fink et al., "An Optically Switched PS-Radar for Pictorial Representation of Object Structures in Human Tissue," Experimentelle Technik De Physik, vol. 38, No. 3, 1990, pp. 197-206, 10 pages.
Office Action dated Feb. 22, 2006 from Related U.S. Appl. No. 10/621,196.
Office Action dated Nov. 14, 2006 from Related U.S. Appl. No. 10/621,196.
Office Action dated Apr. 18, 2007 from Related U.S. Appl. No. 10/621,196.
Office Action dated Sep. 10, 2007 from Related U.S. Appl. No. 10/621,196.
Advisory Action dated Nov. 6, 2007 from Related U.S. Appl. No. 10/621,196.
Office Action dated Feb. 5, 2008 from Related U.S. Appl. No. 10/621,196.
Office Action dated Jul. 10, 2008 from Related U.S. Appl. No. 10/621,196.
Office Action dated Dec. 2, 2008 from Related U.S. Appl. No. 10/621,196.
Office Action dated Jan. 29, 2009 from Related U.S. Appl. No. 11/331,781.
Office Action dated Feb. 25, 2009 from Related U.S. Appl. No. 11/331,944.
Office Action dated Jun. 18, 2008 from Related U.S. Appl. No. 11/331,485.
Office Action dated May 18, 2006 from Related U.S. Appl. No. 10/690,472.
Office Action dated Jan. 30, 2007 from Related U.S. Appl. No. 10/690,472.
Notice of Allowance dated Aug. 6, 2007 from Related U.S. Appl. No. 10/690,472.
Office Action dated Aug. 8, 2008 from Related U.S. Appl. No. 11/140,475.
International Search Report from PCT/US2009/039659, Jul. 6, 2009, 4 pages.
Office Action dated Apr. 28, 2009 From Related U.S. Appl. No. 11/331,485.
Office Action dated Jul. 15, 2009 From Related U.S. Appl. No. 11/331,485.
Office Action dated May 6, 2009 from Related U.S. Appl. No. 11/362,542.
Canadian Office Action for Application No. 2542863, dated Sep. 30, 2010.
Faddis et al., "Novel, Magnetically Guided Catheter for Endocardial Mapping and Radiofrequency Catheter Ablation," Journal of the American Heart Association, Nov. 11, 2002.
International Search Report for PCT/US2010/036149, dated Sep. 29, 2010.
International Search Report for PCT/US2010/052684, dated Dec. 6, 2010.
International Search Report for PCT/US2010/052696, dated Dec. 8, 2010.
International Search Report from PCT/US03/22122, Nov. 6, 2003.
Ishiyama, et al.; Magnetic micromachines for medical applications. Journal of Magnetism and Magnetic Materials. 2002; vol. 242; pp. 41-46.
Materials Library in FEMM 4.0, May 18, 2007, pp. 3-4.
Ritter, et al.; Application of high gradient magnetic separation principles to magnetic drug targeting. Journal of Magnetism and Magnetic Materials. 2004; vol. 280; pp. 184-201.
Standard Specifications for Permanent Magnet Materials, Magnetic Materials Producers Association, 1964.
Totsu, et al.; Three-axis magneto-impedance effect sensor system for detecting position and orientation of catheter tip. Sensors and Actuators. 2004; Issue A 111; pp. 304-309.

SYSTEM AND METHOD FOR A CATHETER IMPEDANCE SEEKING DEVICE

BACKGROUND

1. Field

The invention relates to the placement of catheters in contact with specific anatomical locations while optimizing the direction and orientation of tissue contact.

2. Description of the Related Art

Cardiac rhythm disturbances are a major cause of morbidity and mortality in the adult population. A great deal of progress has been made in the past several decades in the diagnosis and treatment of many of the rhythm disorders of the heart. Intracardiac electrode catheters have been developed for defining the diagnosis of arrhythmias and for delivering ablative energy to specific intracardiac sites. Examples of arrhythmias that are susceptible to treatment with catheter ablation include: atrial fibrillation, atrial flutter, ablation of accessory atrio-ventricular pathways, AV nodal reciprocating tachycardia, ectopic atrial rhythms, ventricular tachycardia arising in either chamber or near the semilunar valves. Because atrial fibrillation is by far the most prevalent significant cardiac arrhythmia in the adult population, and because the ablation of this arrhythmia has become the most common ablation procedure performed in Electrophysiology Laboratories, we will focus our discussion on the putative mechanisms of this arrhythmia and on the various ablation strategies currently utilized for its treatment.

For clinical purposes atrial fibrillation (AF) can be 'paroxysmal', 'persistent' or 'chronic.' Haissaguerre is credited with having made the observation that paroxysmal AF is frequently triggered by a focal 'trigger', most frequently in one of the four pulmonary veins that insert into the left atrium. He further reported that ablation of such a trigger can eradicate paroxysmal AF. In patients with persistent or chronic AF, it appears that atrial 'remodeling' takes place which somehow augments the number of triggers or 'drivers' that initiate and perpetuate AF. In such patients, who, in fact, represent the vast majority of patients presenting with this arrhythmia, the AF 'drivers' are probably located further away from the ostia of the pulmonary veins. It is also thought that the autonomic nervous system plays a role in both paroxysmal and persistent AF, and that ablation at or near ganglionic plexi in the left atrium might be effective in the treatment of AF.

With the above observations in mind, empiric sets of RF lesions have been developed during the past several years. Since paroxysmal AF is thought to be trigger-dependent, circumferential lesions around the ostia of pulmonary veins are thought to be an integral part of the ablation procedure. Electrical isolation of the veins is thought to be critical for containment of the triggers within the veins. For patients with persistent of chronic AF, pulmonary vein isolation is usually also performed, but additional lesion sets are also often created so that the AF substrate is drastically modified, including linear sets of lesion across the 'roof' of the left atrium connecting the two superior pulmonary veins, as well as an 'isthmus' lesion line connecting the left inferior pulmonary vein and the mitral valve annulus. Some physicians also advocate searching for sites in the left atrium which manifest specific electrogram characteristics, such as continuous, low amplitude fragmented signals. Infrequently, the superior vena cava in the right atrium is also electrically isolated, when triggers can be demonstrated to originate from this structure. Finally, in patients who also manifest a typical form of atrial flutter, a line of lesions is often created in the floor of the right atrium, connecting the tricuspid valve annulus to the inferior vena cava.

The foregoing discussion suggests that in order to achieve a therapeutic success with a catheter based ablation procedure, the proper energy source needs to be used, a thorough knowledge of the relevant anatomy needs to be obtained and used during the procedure, the lesions need to be deep enough and sufficiently contiguous in order to prevent electrical conduction at the relevant sites (achieve "isolation" of pulmonary vein ostia), and the catheters need to be able to reach the relevant sites and to remain stable at each site during the delivery of ablative energy.

As noted, in order to safely and effectively perform a left atrial ablation procedure, a detailed understanding of the relevant anatomy is essential. At present, 3D electroanatomic and impedance mapping systems are in use (CARTO, Biosense Webster, and EnSite NavX, St Jude Medical). These systems facilitate the creation of anatomic depictions of the left atrium. Recently, in an attempt to optimize catheter localization, these systems have also evolved to permit the integration of pre-acquired CT and MRI images with real-time 3D maps. One limitation associated with image integration is the potential for chamber wall deformation by catheter pressure on the endocardial surface of the heart; this can result in an inaccurate map and suboptimal image integration. Other limitations of current mapping systems include the occasional creation of anatomic "false spaces", i.e., computer depiction of regions that do not correspond to true anatomic structures.

The potential for serious complications during and after RF ablation in the heart has been well documented. Adverse outcomes can include tissue perforation with resultant pericardial tamponade and systemic shock, formation of thrombi at the site of ablation or on the tip of the catheter, inadvertent damage to important structures such as coronary arteries or the normal conduction system, late formation (1-2 weeks post-procedure) of an esophageal-left atrial fistula. It is likely that these complications are, at least in part, related to inadequate temperature and energy regulation available in current ablation systems.

As described above, it is common to steer the catheter to a specific position which has been referenced to an anatomical location via an acquired map. The static anatomical maps are used to specify either a median position or extreme limit of the moving tissue surface. Under the rigors of cardiac motion (e.g., the Systole/Diastole cycle), the catheter is guided to the specified surface location by synchronizing the average position of the catheter with the average position of the surface location, represented by a point on the anatomical map.

The prior art has been concerned with the placement of the distal portion of the catheter or medical device with respect to the current location and orientation, or with respect to a location on a static geometric map. The prior art has difficulty in acquiring and maintaining continuous tissue contact in the presence of a dynamic moving frame using static positional reference points. Such reference points, comprising the anatomical map, cannot account for the current location of the actual surface.

Where prior art advances a tool to a geometric location, it cannot specify an optimized tool orientation to acquire and maintain contact with a moving surface.

SUMMARY

The system and methods described herein solve these and other problems by enhancing a Catheter Guidance Control and Imaging (CGCI) system by employing relatively high-speed tissue contact information, a closed-loop regulator and a set of heuristic logic routines to aid in acquiring and maintaining tissue contact at or near the specified location on a static geometric map. The actual tissue surface is sought along a path relatively normal to the static geometric surface and passing through the desired geometric target location. In addition, the geometric map information is used to optimize the travel path of the distal portion of the catheter to the surface, as well as optimizing the orientation of the distal tip as to best maintain surface contact.

Moreover, the system and methods described herein correct problems arising from the prior art's inability to assess in a real-time fashion whether or not the catheter is actually in contact with endocardial tissue, the actual pressure exerted by the catheter tip, the actual stability of the catheter on any particular anatomic site, and the absence of a real-time assessment of the size of the lesion being formed during RF application. These systems and method improve over current techniques such as fluoroscopy by providing tactile feed-back to the clinician's hands (the "feel" of the catheter), and/or electrogram characteristics.

By employing relatively real-time tissue contact data in a closed-loop servo system, the map formed by the 3D mapping system (e.g., NavX) creates actual anatomic borders. Confirmation of true and stable electrode-tissue contact allows for employing the lowest amount of energy for safe lesion creation. The improved accuracy of the map allows for excellent stability of the catheter electrode tip-tissue contact, thereby reducing errors in the amount of energy applied to the cardiac surface. Relatively real-time impedance measurement allows for relatively real-time titration of energy delivery using the closed-loop feedback system. It also provides improved travel of the catheter within structures such as, for example, the left atrium, by regulating the rotation of the Lorentz sheath and advancing the catheter in the desired direction while seeking the appropriate tissue impedance data described herein. The system and methods herein improve the accuracy of the generated 3D map while decreasing the time that is required for creation of this map, increase the clinical success rate by assuring the contiguity of the RF lesions (at least in part by enhancing the ability of the catheter to reach all important anatomic sites, and by monitoring the size and depth of the lesions created by RF application), reduce or eliminating complications due to catheter delivery of RF energy by more accurately gauging the pressure exerted by the catheter against the chamber wall, and decreasing the length of time required for these procedures.

In one embodiment, an introducer is inserted into a patient via a vein or orifice, and the distal end guided to the area of interest. A Lorentz Active Sheath (LAS) introducer, as detailed below, is a modified introducer which has embedded electrodes and is thereby detectable by a Lorentz Catheter Position Detection System (CPDS). A catheter is inserted via the LAS sheath and the catheter's distal tip is extended into the area of interest. The proximal ends of the LAS and catheter shaft are attached to the catheter impedance-seeking device's (CISD) mechanical control fixtures. When an anatomical location is selected within the Catheter Guidance Control and Imaging system (CGCI), the invention first uses the geometric map and location information to optimize the workspace and direction of tissue contact by rotating, advancing or retracting the LAS sheath. As the CGCI guides the tool to the desired location, the higher speed tissue impedance-seeking logic attempts to acquire and maintain tissue contact by advancing or retracting the catheter using tip location and contact information. The CGCI system activates the impedance-seeking system whenever it is attempting to reach continuous tissue contact. When contact is made and maintained, the impedance-seeking logic sends the CGCI a continuous-contact signal. When contact is made in the incorrect location on the tissue, the impedance-seeking logic may selectively retract the tip from tissue contact and try again, or it may stop and alert the CGCI as to the amount of error and allow the CGCI to decide what actions to perform next. When an unknown obstacle is encountered far from the expected tissue surface, the impedance-seeking logic will alert the CGCI system to plan a path around the obstacle.

The Lorentz-Active Sheath (LAS), serves as a conduit for other medical devices, such as catheters, balloons, biopsy needles, etc. The sheath is inserted into a vein or other body orifice and is guided into the area where the operation is to be performed. The position and orientation of the LAS is tracked via a position detection system which emits electrical signals that are sensed through several electrodes coupled to the LAS. The signals received from the LAS are used to calculate an accurate and reliable assessment of the actual position of the LAS within the patient.

The Catheter Position Detection System (CPDS) can be a conventional Lorentz positioning system, such as, for example, the EnSite system from St. Jude Medical Inc. Atrial Fibrillation Division, which sends electrical signals through patches placed upon the patient. These electrical signals are detected through electrodes on the surface of the catheters, giving the position of each electrode.

The Tissue Contact Detector is a Lorentz positioning system accessory device which differentiates between the impedance signals from tissue contact and blood-pool contact. The Tissue Contact Detector operates inside of the CPDS system, and is electrically connected to the distal electrode of the catheter.

The CGCI (Catheter Guidance Control and Imaging) uses the Catheter Position Detection System (CPDS) information and a magnetic chamber to push, pull, and steer a magnetically-tipped catheter. The operator uses a virtual tip controller to specify a desired catheter position and orientation, DP, in the CGCI. The CGCI directs the tip to DP using the actual position and orientation of the catheter, AP, which is received from the CPDS. In one embodiment, the CGCI system includes a system whereby a magnetic tip attached to a surgical tool is detected, displayed and influenced positionally so as to allow diagnostic and therapeutic procedures to be performed rapidly, accurately, simply, and intuitively. The tools that can be so equipped include catheters, guidewires, and secondary tools such as lasers and balloons, in addition biopsy needles, endoscopy probes, and similar devices. The magnetic tip allows the position and orientation of the tip to be determined by analyzing a magnetic field (with or without supplemental use of other systems, such as, for example, x-rays, ultrasonics, etc.). The magnetic tip further allows the tool tip to be pulled, pushed, turned, and forcefully held in the desired position by applying an appropriate magnetic field external to the patient's body. A Virtual Tip (a multi-axis joystick-like device providing up to six degrees of freedom or more) serves as an operator control. Movement of the operator control produces corresponding movement of the magnetic tip inside the patient's body. Additionally, the control provides tactile feedback to the operator's hand in the appropriate axis or axes if the magnetic tip encounters an obstacle. The output of the control combined with the magnetic tip position and orientation feedback allows a servo system to control the external magnetic field by pulse width modulating the positioning electromagnet. Data concerning the dynamic position of a moving body part, such as a beating heart, offsets the servo systems response in such a way that the magnetic tip, and hence the secondary tool is caused to move in unison with the moving body part. The tip position and orientation information and the dynamic body part position information are also utilized to provide a display that allows three dimensional viewing of the magnetic tip position and orientation relative to the body part. In one embodiment, an amount of tactile feedback is computed based at least in part on a difference between a desired position and an actual position of the catheter tip position. In one embodiment, tactile feedback is provided as a feedback vector computed based on a difference between a desired position vector (e.g., desired position and orientation) of the catheter tip and an actual position vector (e.g., actual position and orientation) of the catheter tip. Thus, when provided as a feedback vector, tactile feedback can be different as the virtual tip is moved in different directions (e.g., in connection with the different degrees of freedom). In one embodiment, tactile feedback is filtered to reduce noise. In one embodiment, tactile feedback is threshold filtered such that errors below a certain threshold do not produce tactile feedback.

In another embodiment, the Catheter Position Detection System (CPDS) is the CGCI Magnetic Catheter Position Detection System, including a method and apparatus for detecting position and orientation of catheter distal magnetic element while it moves in a patient's heart. In one embodiment, the apparatus includes four or more sensors for detecting the magnetic field generated by the catheter tip. The sensors transmit the field magnitude and direction to a detection unit, which filters the signals and removes other field sources, such as generated by CGCI coils and external medical hardware. The method allows the measurement of magnitude corresponding to the catheter tip distance from the sensor and the orientation of the field showing the magnetic tip orientation. Since the tip's magnetic field is not symmetric, the position and orientation computation technique are not independent of each other. Hence, an iterative calculation is used to converge to a solution. The method of determining tip position is calculated by triangulation from each sensor, and whereby the tip orientation is calculated by an intersecting-planes algorithm. The orientation is used to adjust the distances from each sensor, and the process is repeated until convergence for both position and orientation is achieved. The resultant value provides the actual catheter tip position and orientation (AP). The actual position is further filtered by synchronizing the AP measurements with the QRS signal of the heart, allowing the operator and CGCI controller to view the organ as a static object.

In one embodiment, a controllable magnetic field source produces a magnetic field to guide a tool (e.g., catheter, introducer, Lorenz sheath, guidewire, etc.) having a distal end responsive to the magnetic field. One or more sensors are configured to sense a current vector position of the distal end by measuring one or more impedances. A controller controls the magnetic field source to control a movement of the distal end according to a feedback calculation wherein the system controller is configured to compute a position error comprising a difference between a desired vector position of the distal end and the current vector position of the distal end. An operator control is used to provide tactile feedback to an operator when the position error exceeds a predetermined amount, wherein the tactile feedback is computed by the controller at least in part according to the vector position error. In one embodiment, a correction input to the desired vector position is computed based on a position of a heart relative to a frame of reference, such that the system controller compensates for a dynamic position of a wall of a heart chamber such that the distal end maintains contact with the wall of the heart chamber at least in part by measuring at least one impedance between the distal end and the wall. In one embodiment, the tool includes a Lorenz sheath.

In one embodiment, one or more patches are provided to the patient, wherein the apparatus measures a position and orientation of a Lorenz sheath at least in part by measuring one or more impedances between the Lorenz sheath and the conductive patches.

In one embodiment, the controller is configured to control the magnetic field source to maintain the distal end in a desired vector orientation relative to the wall (e.g., an interior wall of a heart chamber, artery, vein, or other anatomical structure). In one embodiment, the controller is configured to control the magnetic field source to maintain the distal end substantially normal to the wall. In one embodiment, the controller is configured to differentiate between contact with the wall and contact with an obstruction by analyzing differences between a measured impedance and an expected impedance. In one embodiment, the controller is configured to compute a path around the obstruction. In one embodiment, the controller is configured to control the magnetic field source to maintain the distal end in a desired orientation relative to the wall. In one embodiment, the controller is configured to differentiate between contact with the wall and contact with other tissue by analyzing differences between a measured impedance and an expected impedance, the expected impedance corresponding to the wall. In one embodiment, the other tissue includes a blood pool.

In one embodiment, the controller is configured to seek contact with the wall by calculating a target manifold, monitoring a distal end-to-target vector with respect to the target manifold, calculating a new tool length, and adjusting a length of the tool according to the new tool length.

In one embodiment, the tool includes an introducer. In one embodiment, the controller controls a rotation and translation of the introducer.

In one embodiment, a method for positioning a surgical tool and maintaining relatively continuous contact between a distal end of the tool and a desired tissue location, includes controlling a position and orientation of a distal end of a surgical tool by adjusting currents in a plurality of electromagnets, measuring a plurality of impedance values between the distal end and a plurality of tissue locations, constructing an impedance map at least in part form the plurality of impedance values, determining a first impedance value corresponding to an impedance measured when the distal end touches the desired tissue location, and using a feedback controller to control the currents to maintain contact between the distal end and the desired tissue such that the distal end is oriented relatively normal to the desired tissue location in the presence of motion of the desired tissue location, wherein feedback information to the feedback controller includes periodic impedance measurements between the distal end and the desired tissue location.

In one embodiment, the method further includes, computing a position error comprising a difference between a desired vector position of the distal end and the current vector position of the distal end, and providing tactile feedback to an operator control when the position error exceeds a predetermined amount, wherein the tactile feedback is computed at least in part according to the position error.

In one embodiment, the method includes locating the distal end by measuring impedances between a plurality of patches provided to the patient and the surgical tool.

In one embodiment, the method includes differentiating between contact with the desired tissue location and contact with an obstruction by analyzing differences between a measured impedance and an expected impedance. In one embodiment, the method includes computing a path around the obstruction.

In one embodiment, the method includes distinguishing between contact with the desired tissue location and contact with other tissue by analyzing differences between a measured impedance and an expected impedance, the expected impedance corresponding to an impedance at the desired tissue location. In one embodiment, the other tissue includes a blood pool.

In one embodiment, the method includes seeking contact with the desired tissue location by calculating a target manifold, monitoring a distal end-to-target vector with respect to the target manifold, calculating a new tool length, and adjusting a length of the tool according to the new tool length. In one embodiment, the tool includes an introducer. In one embodiment, the method includes controlling a rotation and translation of the tool.

DETAILED DESCRIPTION

Figure 1:
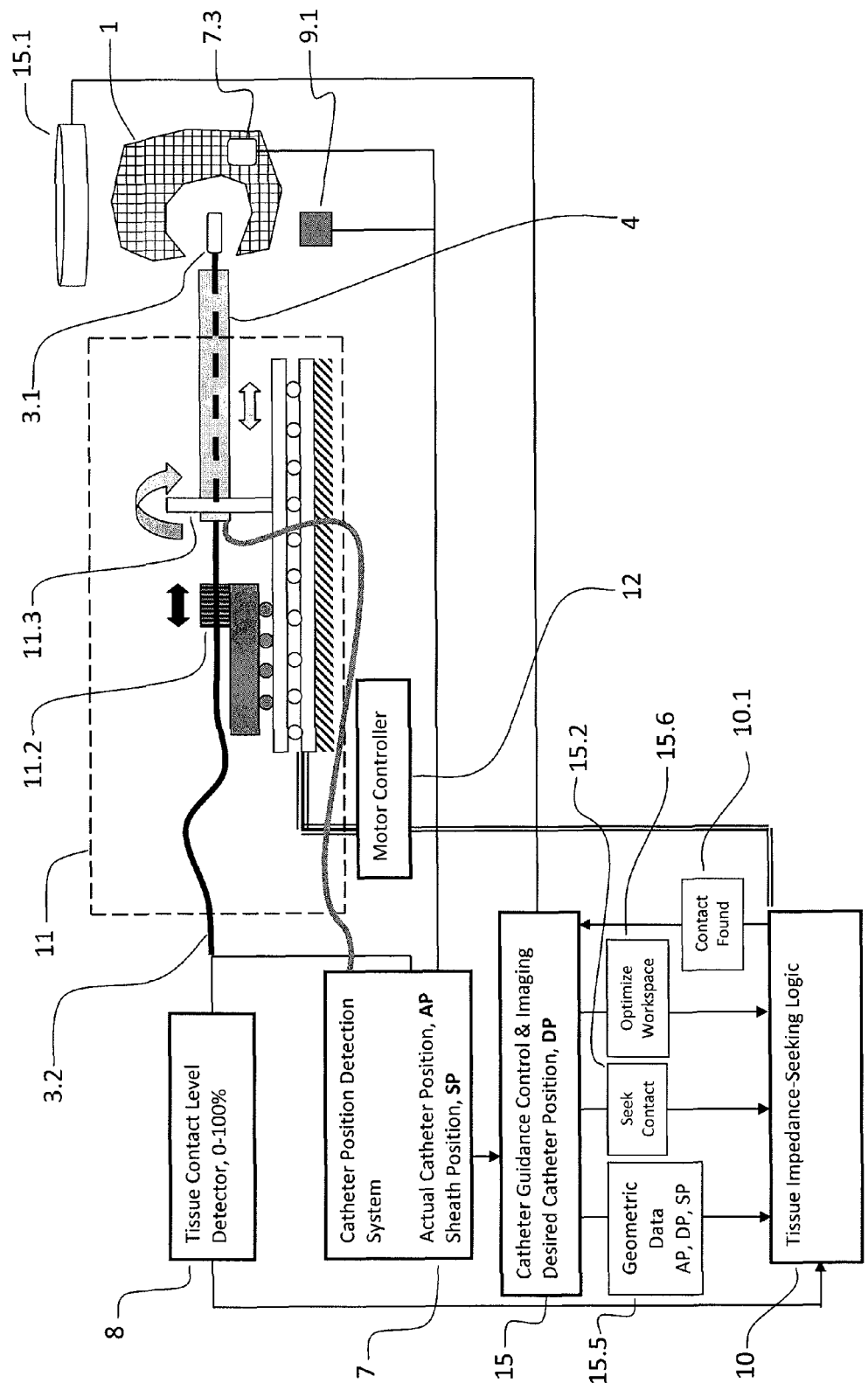
FIG. 1 is a schematic diagram of the signals and systems used in tissue impedance seeking.

FIG. 1 is a schematic diagram of the signals and systems used in tissue impedance seeking. A catheter 3 is inserted through a sheath (LAS introducer) 4 and into a patient 1. A catheter tip 3.1 is advanced into the patient and a catheter shaft 3.2 is connected within a CISD Mechanical Assembly 11 to a Catheter Shuttle 11.2. The proximal portion of the LAS sheath 4 is provided to a Sheath Shuttle 11.3. The proximal end of the catheter shaft 3.1 is connected to both the Tissue Contact Level Detector 8 and a Catheter Position Detection System (CPDS) 7 by the catheter electrical connector. The sheath position and orientation, SP 40, is also detectable by the CPDS 7, so the sheath 4 is also provided to the CPDS 7 by an electrical connector. The Catheter Position Detection System 7 uses the signals from the catheter and from the Catheter Position Detection System Patches 7.3, placed on the patient 1, to determine catheter position and orientation, which is passed on to the Catheter Guidance Control and Imaging System (CGCI) 15. In this embodiment, the CGCI 15 uses electromagnets 15.1 to push, pull and steer the catheter tip 3.1 within the patient 1. The CGCI 15 operates in a closed-loop regulation mode with the Catheter Position Detection System 7 to synchronize the Desired Position and Orientation, DP 30, of the catheter tip 3.1 with the Actual Position and Orientation, AP 20, of the catheter tip 3.1. When the CGCI 15 is directed by the operator to seek a location on the tissue surface at or near DP 30, the CGCI sends the Tissue Impedance-Seeking Logic routines 10 the Geometric Target Distance vector 15.1, the Geometric Normal Vector 15.3 (shown in FIG. 3) for tissue contact direction, and a command to Seek Tissue Contact 15.2. The Tissue Impedance Seeking Logic 10 uses the CISD Motor Controller 12 to extend or retract the sheath 4, rotate the sheath, or extend or retract the catheter 3 in cooperation with the CGCI's magnetic regulation. When continuous tissue contact is detected from the Tissue Contact Detector 8, and the contact is along the Geometric Normal Vector 15.3 which passes through the Geometric Target Position 15.4, the Tissue Impedance-Seeking Logic sends a Contact Found signal 10.1 to the CGCI 15. The Tissue Impedance-Seeking Logic 10 contains routines that optimize the direction of tissue contact, detect obstructions and provide the CGCI 15 additional geometric information about the tissue surface. In an alternate embodiment, the Catheter Position Detection System (CPDS) is the CGCI Magnetic Catheter Position Detection System which uses a set of magnetic sensors 9.1 to determine catheter tip position and orientation, as described later in this document.

Figure 2:
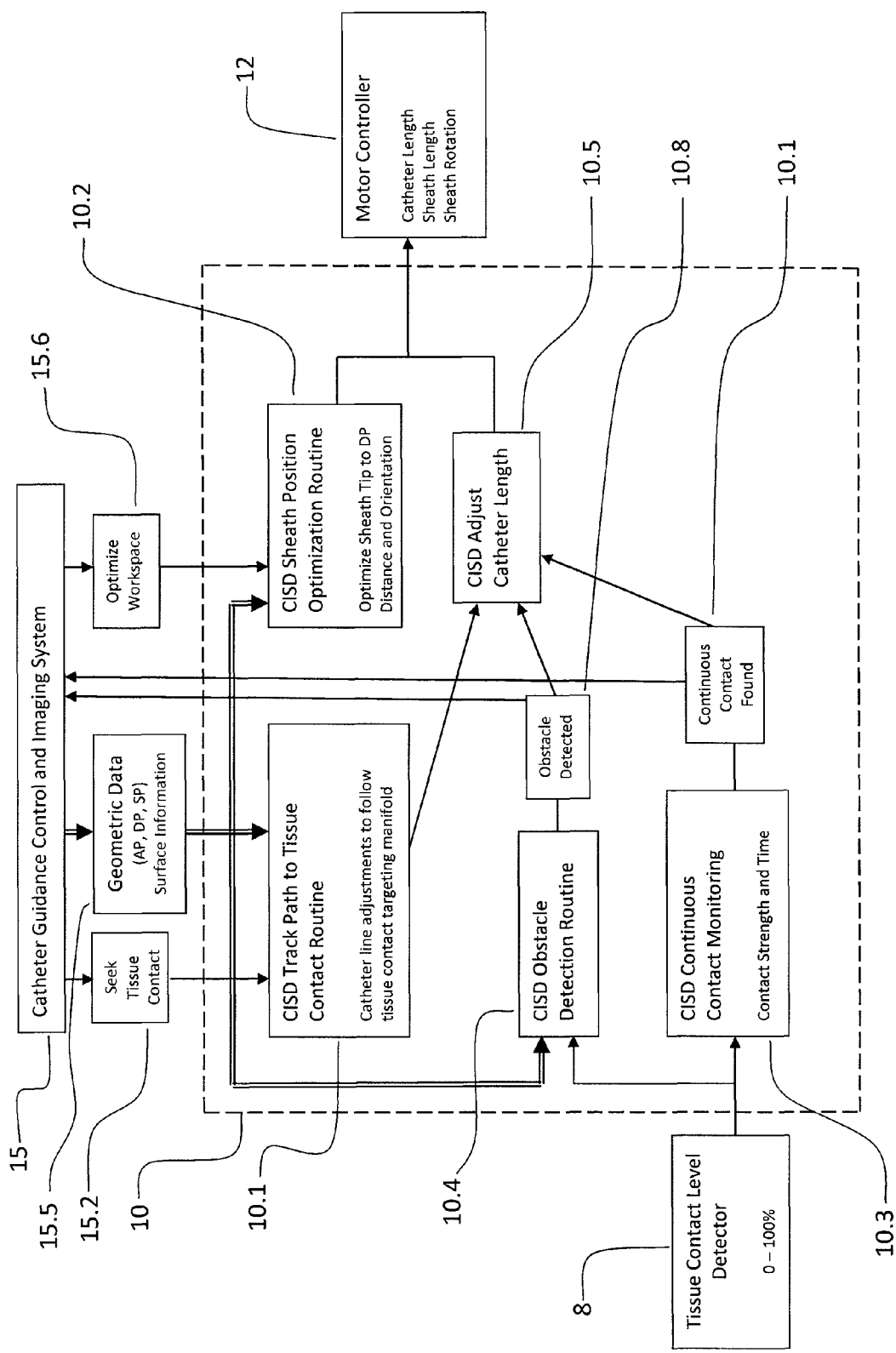
FIG. 2 is a block diagram of the Tissue Impedance-Seeking Logic.

FIG. 2 is a block diagram of the Tissue Impedance-Seeking Logic 10. The Catheter Guidance Control and Imaging System 15 provides the Tissue Impedance-Seeking Logic 10 with the Geometry Normal Vector 15.3, Actual Catheter Position and Orientation, AP 20, Desired Catheter Position and Orientation, DP 30, Sheath Position and Orientation, SP 40, and commands to Seek Tissue Contact 15.5 and Optimize Workspace 15.6. The Tissue Impedance-Seeking Logic routines use the geometric information to calculate a Tissue Contact Manifold 10.7 (see FIG. 3), which is a volume of expected tissue contact extending through the Desired Catheter Position, DP 30, in the direction of the Geometry Normal Vector

15.3. The Tissue Impedance-Seeking Logic routines 10 provide the CGCI 15 with live tissue contact information 8.1, as well as a Continuous Contact Found signal 10.6, which indicates that the catheter has had continuous contact with the surface with the specified contact strength and for the desired length of time. When Continuous Contact Found 10.6 occurs outside of the Tissue Contact Manifold 10.7, the CISD Obstacle Detection Routine 10.4 signals the CGCI that a new path to tissue contact will be specified.

Figure 3:
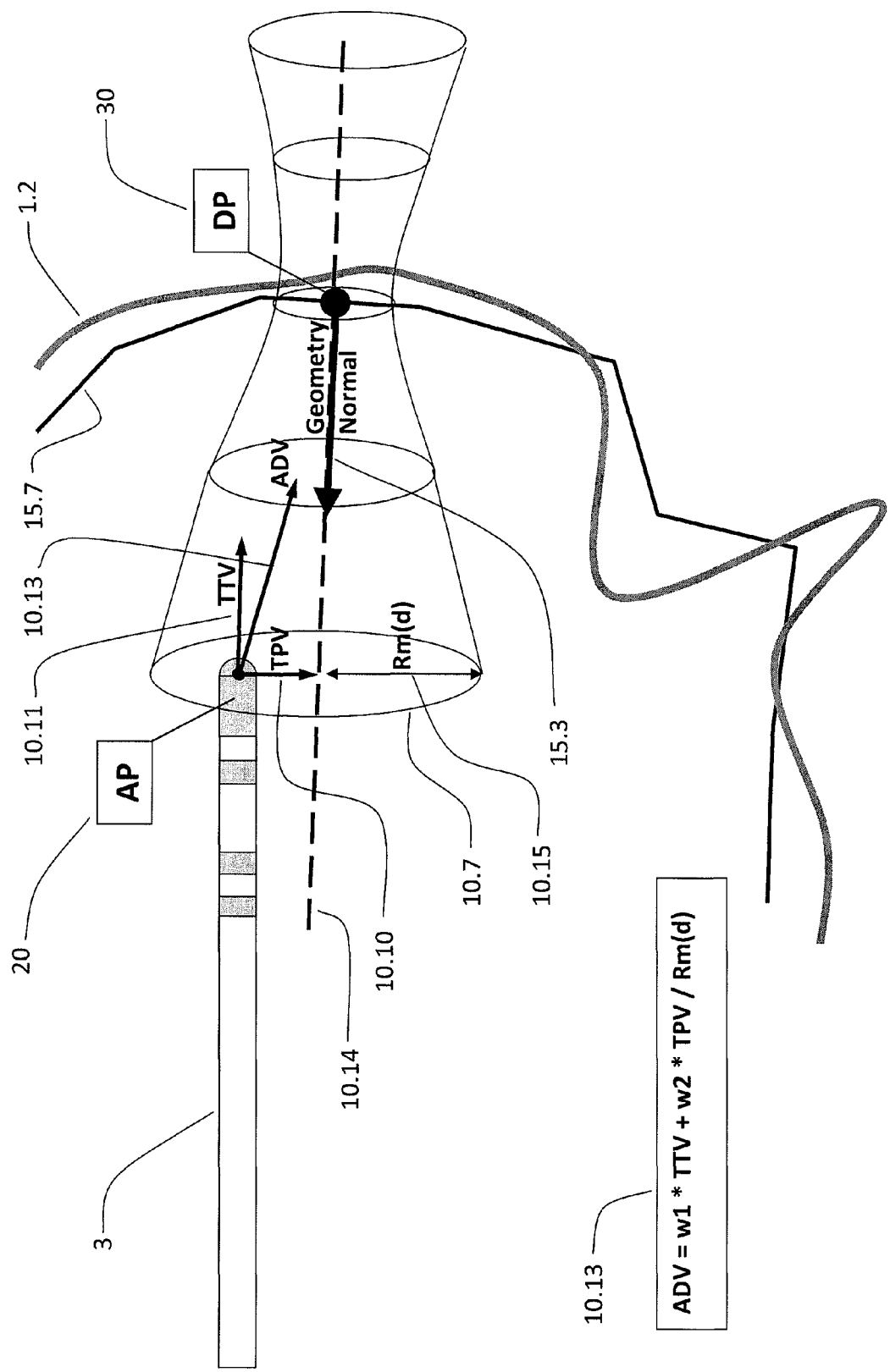
FIG. 3 is a schematic diagram of a catheter in relationship to the virtual and real tissue surface with associated control vector information.

FIG. 3 is a schematic diagram of a catheter in relationship to the virtual and real tissue surface with associated control vector information. The Catheter 3 is guided by the Catheter Guidance Control and Imaging System 15 from its current Actual Position and Orientation, AP 20, through the Desired Position and Orientation, DP 30. DP 30 is on the surface of the CGCI's Geometric Map 15.7, and not on the actual Patient Tissue Surface 1.2, so the catheter is guided on a path to the surface, called the CISD Tissue Contact Targeting Manifold 10.7 until it makes continuous contact with the tissue surface, as indicated by the Tissue Contact Detector 8. The CPCS Normal Vector 15.3 at DP 30 gives the position and orientation of the CISD Tissue Contact Targeting Manifold 10.7. If the Continuous Contact Found 10.6 signal is located outside of the CISD Tissue Contact Targeting Manifold 10.7, the Catheter Impedance-Seeking Logic 15 will signal the CGCI system and a new path will be planned to the tissue surface. The CISD Tissue Contact Targeting Manifold 10.7 shape, size and orientation with respect to the CPCS Normal Vector 15.3 may all be adjusted for desired accuracy. The CISD Tissue Contact Targeting Manifold 10.7 is a set of radius values for the targeting manifold at each distance from the desired position, DP 30. Rm(d) 10.15 may be defined as any function of distance, d, or by an array:

$$Rm(d) = d^2/10 + 2$$

Or: $Rm(d) = 2 + d/4$

Or: $Rm(d) = \{2,3,4,4,5,6,\ldots\}$ for all integers $d$, 0 to $n$

Or: $Rm(d) = 4$ (etc.) 10.15

The tip-to-tissue vector, TTV 10.11, is the negative of the geometric normal vector 15.3 times the magnitude of the distance to DP 30.

$$TTV = -GNV * |DP - AP| \qquad 10.11$$

The tip to path vector, TPV 10.10, is the vector distance from the catheter tip to the tissue path 10.14 passing through DP 30.

$$TPV = GNV * |AP - DP| * [((AP-DP)/|AP-DP|\cdot GNV)] - (AP-DP) \qquad 10.10$$

|TPV| is limited to the values 0 to Rm(d).

The advance vector, ADV 10.13, is the weighted sum of TPV and TTV using the weighting values w1 10.16 and w2 10.17, which may be adjusted for system performance and anatomical location.

$$ADV = w1 * TTV + w2 * TPV * [|TPV|/Rm(d)]/|TPV| \qquad 10.13$$

Which yields: $ADV = w1 * TTV + w2 * TPV/Rm(d)$

The advance vector ADV 10.13 is then used in cooperation with the CGCI 15 to guide the catheter to tissue contact. The CGCI 15 regulates the magnetic field based on the component of ADV perpendicular to the catheter tip axis 901, and the CISD 11 advances the tip based on the component of ADV which is parallel to the catheter tip axis 901.

Figure 4A:
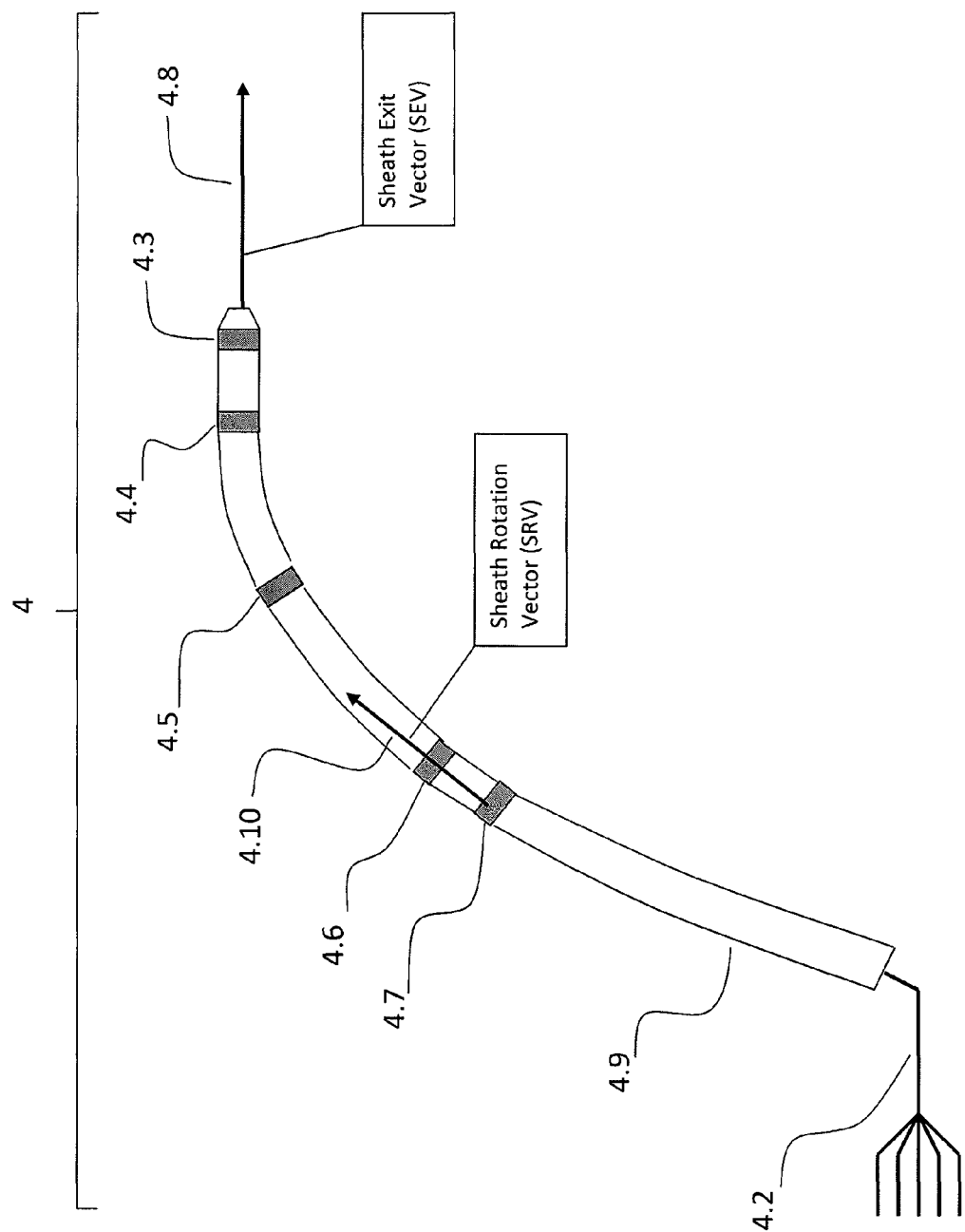
FIG. 4A is an isometric diagram of the Lorentz-Active Sheath (LAS) assembly and the associated vectors used in workspace optimization.

FIG. 4A is an isometric diagram of the Lorentz-Active Sheath (LAS) assembly 4 and the associated vector used in workspace optimization. The Lorentz detection system-sensitive electrodes 4.3-4.7 are integrated into the LAS shaft 4.9 and connected via embedded wires 4.2 to a coupling connector. The electrodes 4.3-4.7 are used to sense electrical signals generated by a Catheter Position Detection System 7. The two most distal electrodes 4.3 and 4.4 are used to determine tool exit position and tool exit direction, SEV 4.8. The two most proximal electrodes 14 and 15 are used to determine the LAS sheath rotation axis vector, SRV 4.10.

Figure 4B:
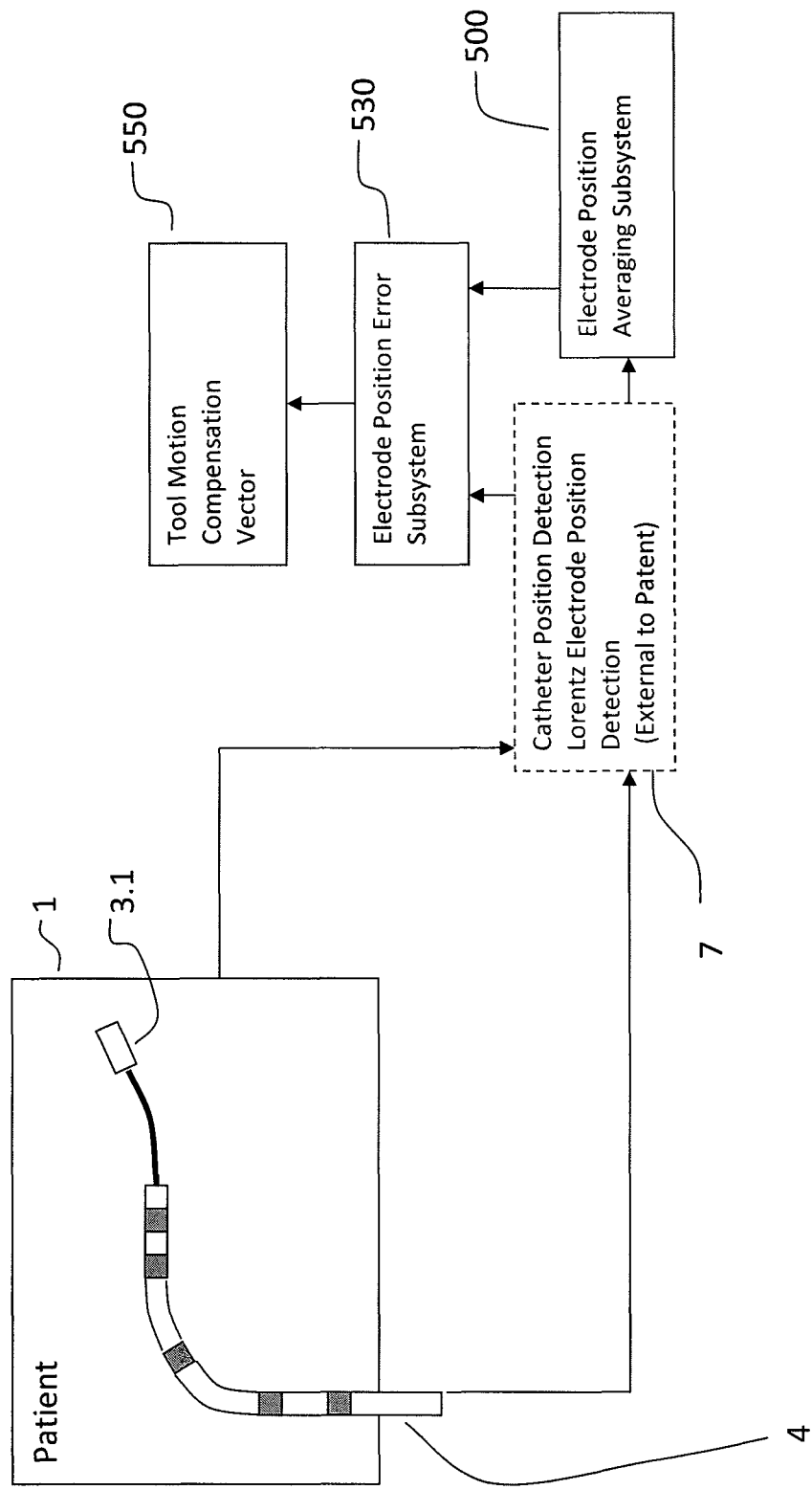
FIG. 4B is a block diagram of the signals and systems used to determine the position of the LAS Electrodes.

FIG. 4B is a block diagram of the signals and systems used to determine the position of the LAS Electrodes 4.3-4.7. In this embodiment, the LAS 4 is inserted in the patient 1 via a vein or orifice and electrically connected to the Catheter Position Detection System 7. The LAS-hosted tool 3 is inserted through the LAS and also connected to the Catheter Position Detection System 7. The position of each electrode 4.3-4.7 is provided by the Catheter Position Detection System via a conventional communications link. One of ordinary skill in the art can use these electrode positions to determine the tool exit position and tool exit direction, SEV 4.8 and sheath rotation axis, SRV 4.10. In this embodiment, the tool exit position and tool exit direction SEV 4.8 are averaged in the Electrode Position Averaging Subsystem 500 and subtracted from the current tool exit position and tool exit direction 4.8 in the Electrode Position Error Subsystem 530 to give a Tool Motion Compensation Vector 550, which is used to remove the LAS motion from the LAS-hosted tool's 3 position. The sheath rotation axis SRV 4.10 aids in determining the motion of the sheath's distal end and tool position while rotating the sheath.

Figure 5:
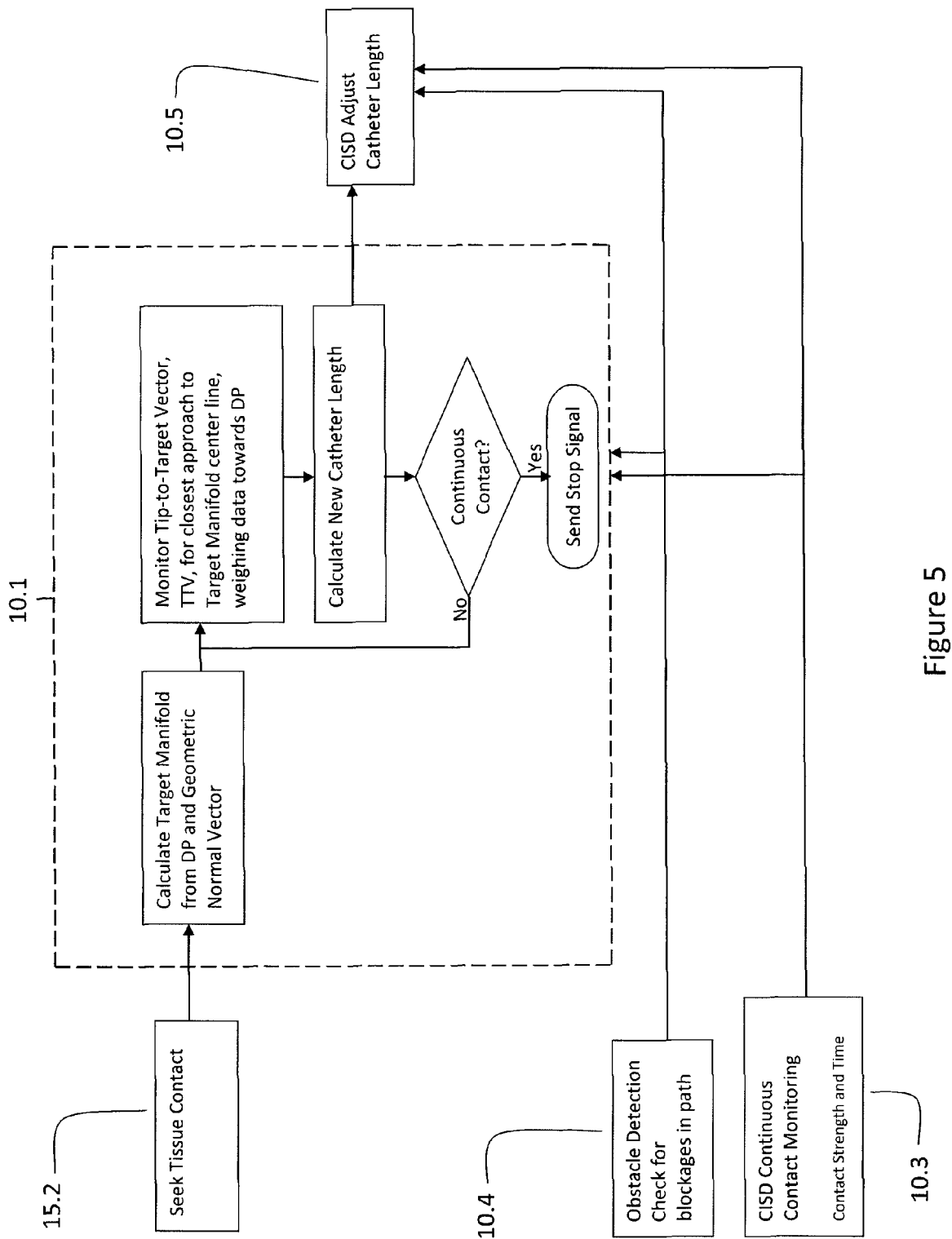
FIG. 5 is a logic flow diagram of the CISD Track Path to Tissue Contact routine.

FIG. 5 is a logic flow diagram of the CISD Track Path to Tissue Contact routine 10.1. The Seek Tissue Contact Signal 15.2 from the CGCI 7 begins the monitoring of the catheter tip position, AP 20, with respect to the Target Manifold 10.7. On a regular time interval, the catheter length is recalculated as to progress the catheter tip 3.1 down through the Target Manifold 10.7 until the Continuous Contact Monitoring routine 10.3 has determined that the tip is in continuous tissue contact. Signals from the Obstacle Detection routine 10.4 may also interrupt the CISD Track Path to Tissue Contact routine 10.1 when the CGCI 15 is used to steer around an unexpected surface contact.

Figure 6:
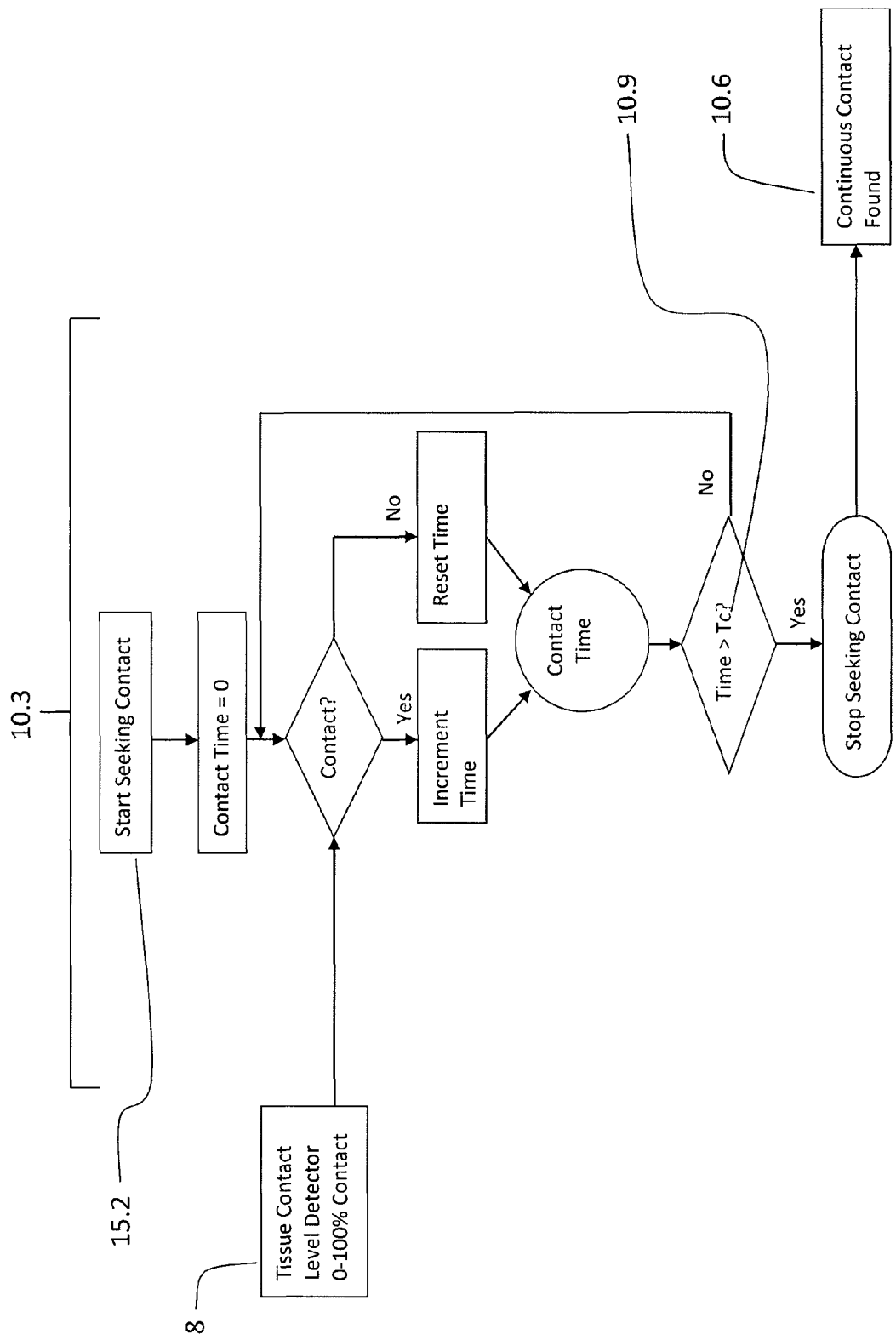
FIG. 6 is a logic flow diagram of the CISD Continuous Contact Monitoring routine.

FIG. 6 is a logic flow diagram of the CISD Continuous Contact Monitoring routine 10.3. When the Seek Tissue Contact command 15.2 is sent from the Catheter Guidance Control and Imaging system 15, the CISD Continuous Contact Monitoring routine 10.3 seeks a period of continuous contact which is greater than the time (Tc) 10.9. When this condition is met, the Continuous Contact Found signal 10.6 is sent to all monitoring systems.

Figure 7:
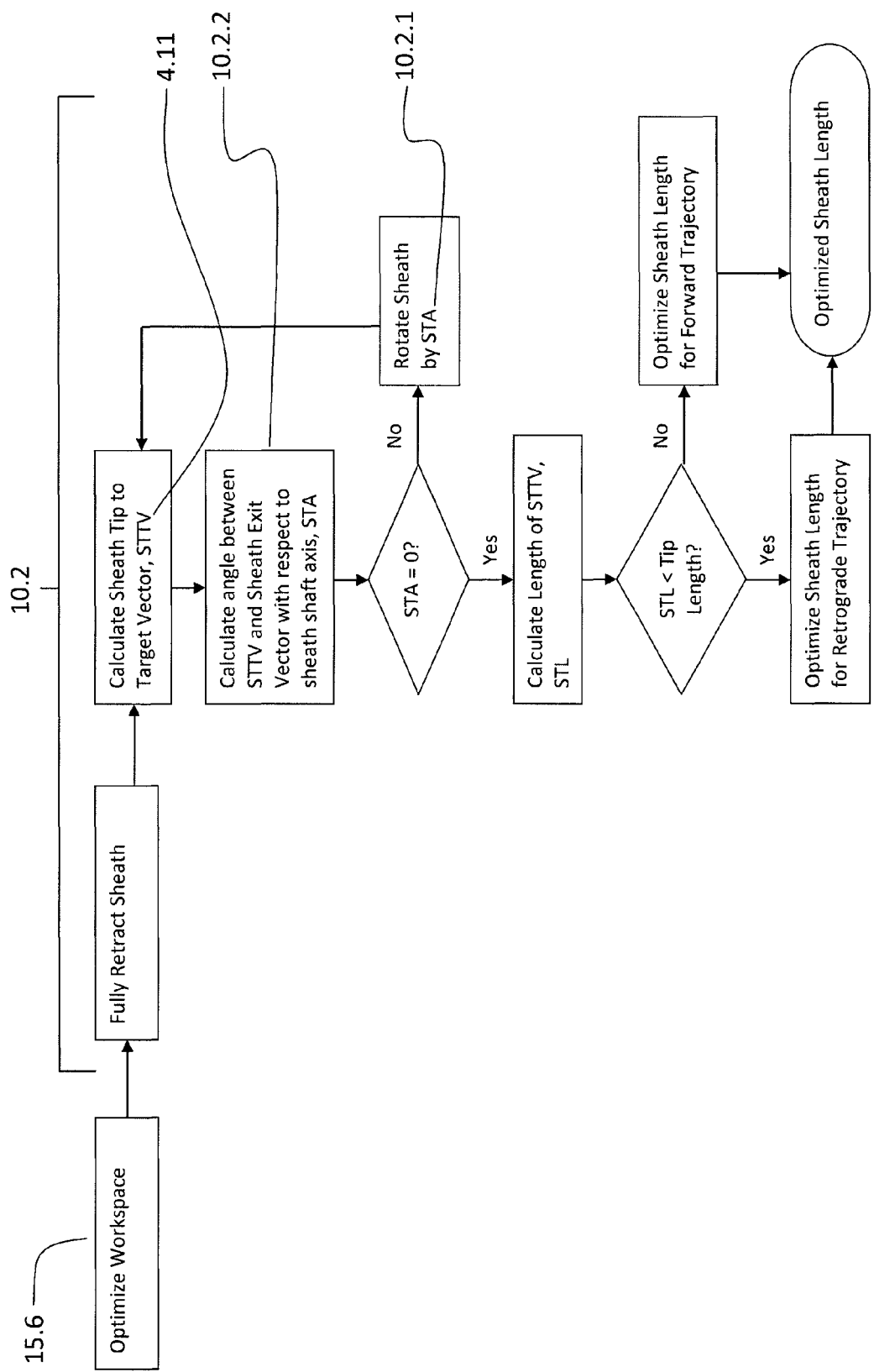
FIG. 7 is a logic flow diagram of the CISD Sheath Position Optimization routine.

FIG. 7 is a logic flow diagram of the CISD Sheath Position Optimization routine 10.2. The sheath 4 begins in a fully-retracted position. The sheath is first rotated, within certain geometric chamber limits, to optimize the alignment between the sheath exit vector, SEV 4.8 and the sheath-tip-to-target direction vector, STTV 4.11. The sheath insertion length is then adjusted depending upon whether the tissue contact may be reached directly, or is to be reached in retrograde fashion, steering the catheter tip 3.1 beyond 90 degrees from the sheath exit vector SEV 4.8. If the retracted sheath-tip-to-target vector length is shorter than the length of the catheter tip 3.1, or if the desired position, DP 30, requires a STTV beyond 90 degrees from the SEV 4.8, the target is considered retrograde.

Figure 8:
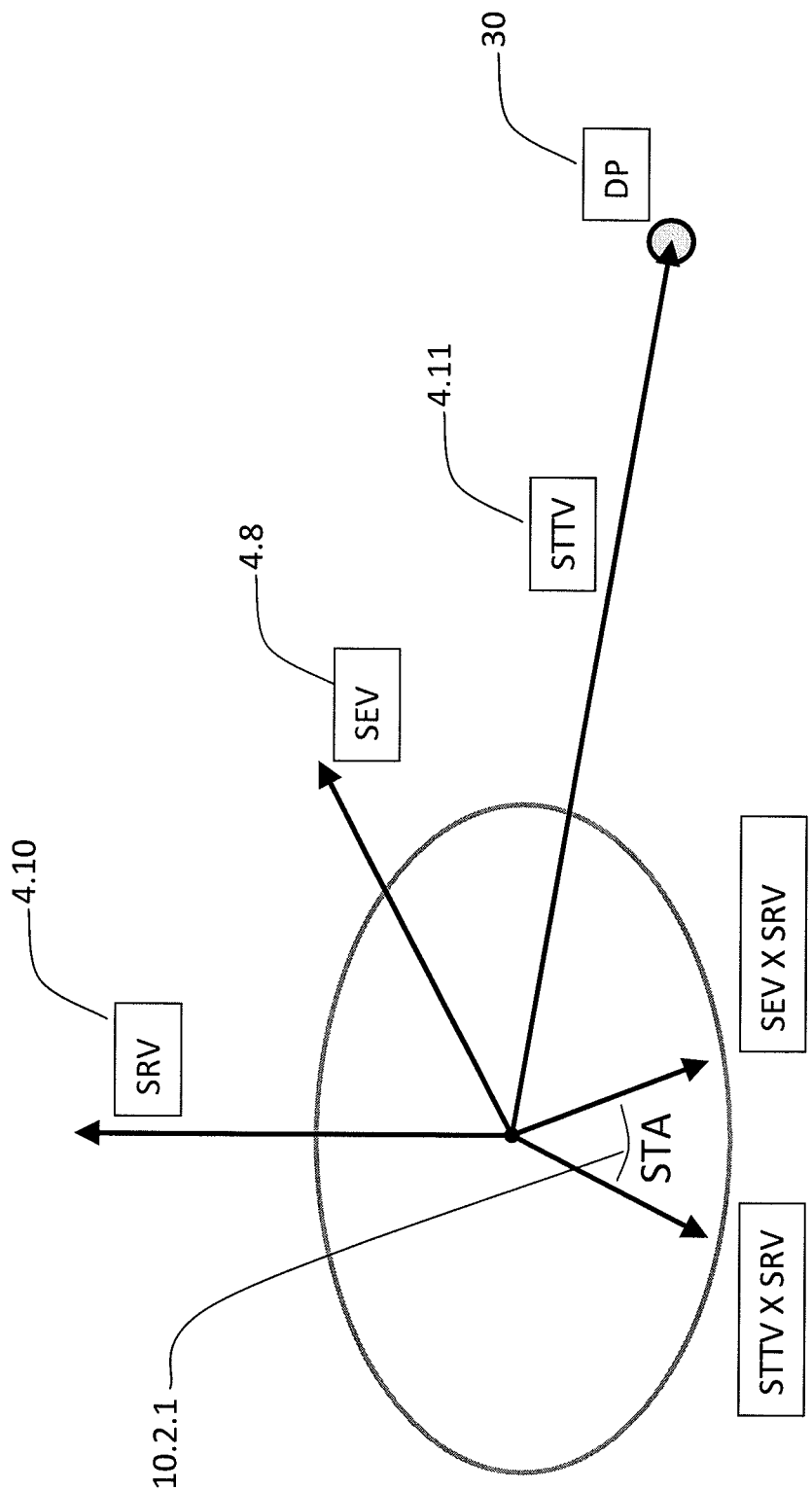
FIG. 8 is a vector diagram of the sheath rotation angle calculation.

FIG. 8 is a vector diagram of the sheath rotation angle calculation. The sheath targeting angle, STA 10.2.1 is on a plane orthogonal to the sheath rotation vector SRV 4.10. STA is defined by the following calculation, which the angle between the cross-products of the sheath rotation vector SRV 4.10 with the sheath exit vector SEV 4.8 and sheath-to-target vector STTV 4.11.

$$STA = A\ COS[((STTV \times SRV)/|STTV||SRV||STTV \times SRV| \cdot (SEV \times SRV)/|SEV||SRV||SEV \times SRV|] \quad (10.2.2)$$

This value is evaluated by heuristic logic routines to account for the orientation of the STTV 4.11.

Figure 9A:
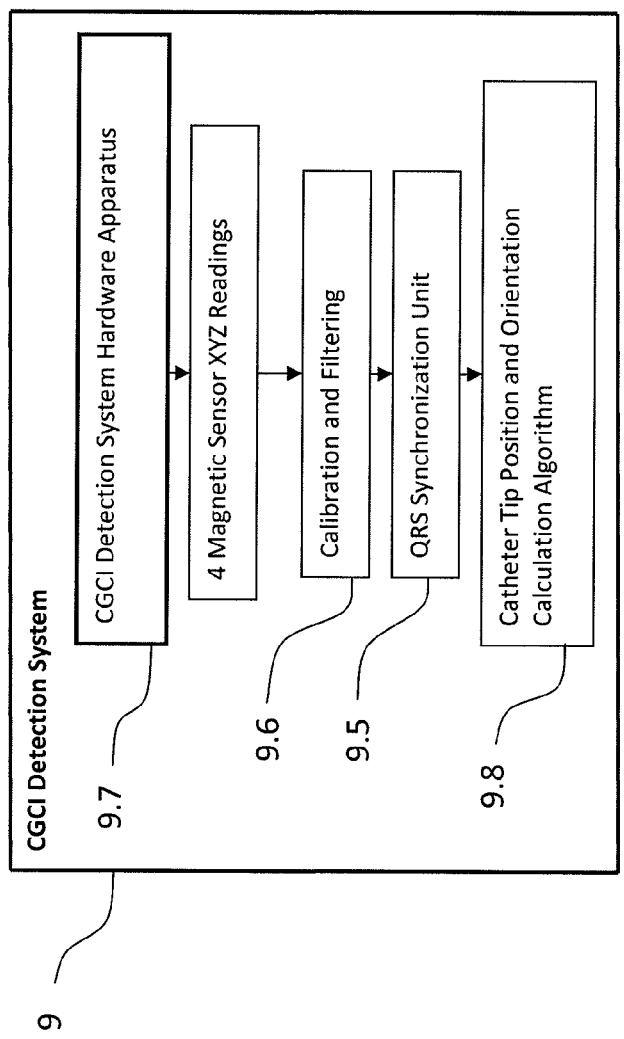
FIG. 9A is a block diagram of the CGCI Position Detection System.

FIG. 9A is a block diagram of the CGCI Position Detection System 9. The CGCI Detection System Hardware 9.7, including four 3-axis Hall-Effect magnetic sensors 9.21-9.24, amplifiers and associated data acquisition connections, sends four magnetic sensor readings 9.1-9.4 to the CGCI Calibration and Filtering software routines 9.6, where background magnetic fields are subtracted. The CGCI QRS Synchronization Unit 9.5 may then be used to synchronize the readings to the most stable portion of the heartbeat, using a sampling window offset from the heartbeat R-peak signal. The four filtered magnetic field vectors are then used by the Catheter Tip Position and Orientation Calculation Algorithm 9.8 to determine the position and orientation of the magnetic catheter tip 3.1.

Figure 9B:
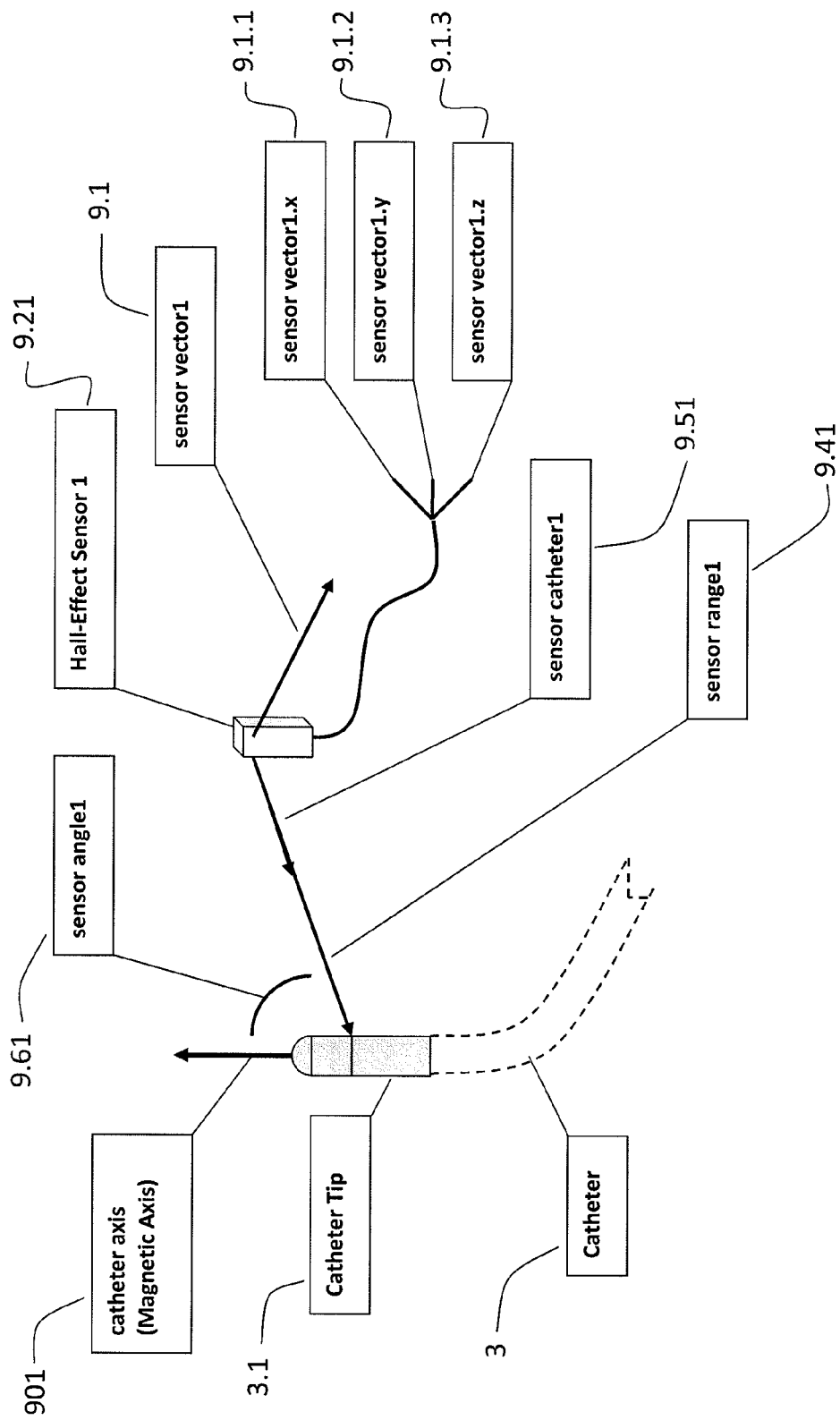
FIG. 9B is a schematic diagram of a Hall-Effect sensor in relationship to the catheter tip, and its generated measurement data.

FIG. 9B is a schematic diagram of a Hall-Effect sensor in relationship to the catheter tip, and its generated measurement data. The catheter 3 and its magnetic tip 3.1 are shown in proximity to Hall-Effect sensor number one 9.21, which is connected through the CGCI Position Detection System hardware (not shown) to provide the three magnetic sensor readings 9.1.1-9.1.3 representing the magnetic field components of magnetic sensor vector number one 9.1 in the X, Y, and Z Cartesian directions at the sensor's location. The other three magnetic sensors are defined as 9.22, 9.23, and 9.24 with sensor vectors 9.2, 9.3, and 9.4 respectively. The catheter tip axis is identical to the catheter tip magnetic axis 901, (which is the directional component of the six-degree of freedom Actual Position, AP 20) and the angle between the catheter tip axis and the direction vector from sensor 1-4 9.21-9.24 to the catheter tip 3.1 is defined as SensorAngle1-SensorAngle4 9.61-9.64. The distances from magnetic sensor 1-4 to the catheter tip are defined as SensorRange1-SensorRange4 9.41-9.44, which have unit direction vectors SensorCatheter1-SensorCatheter4 9.51-9.54.

Figure 9C:
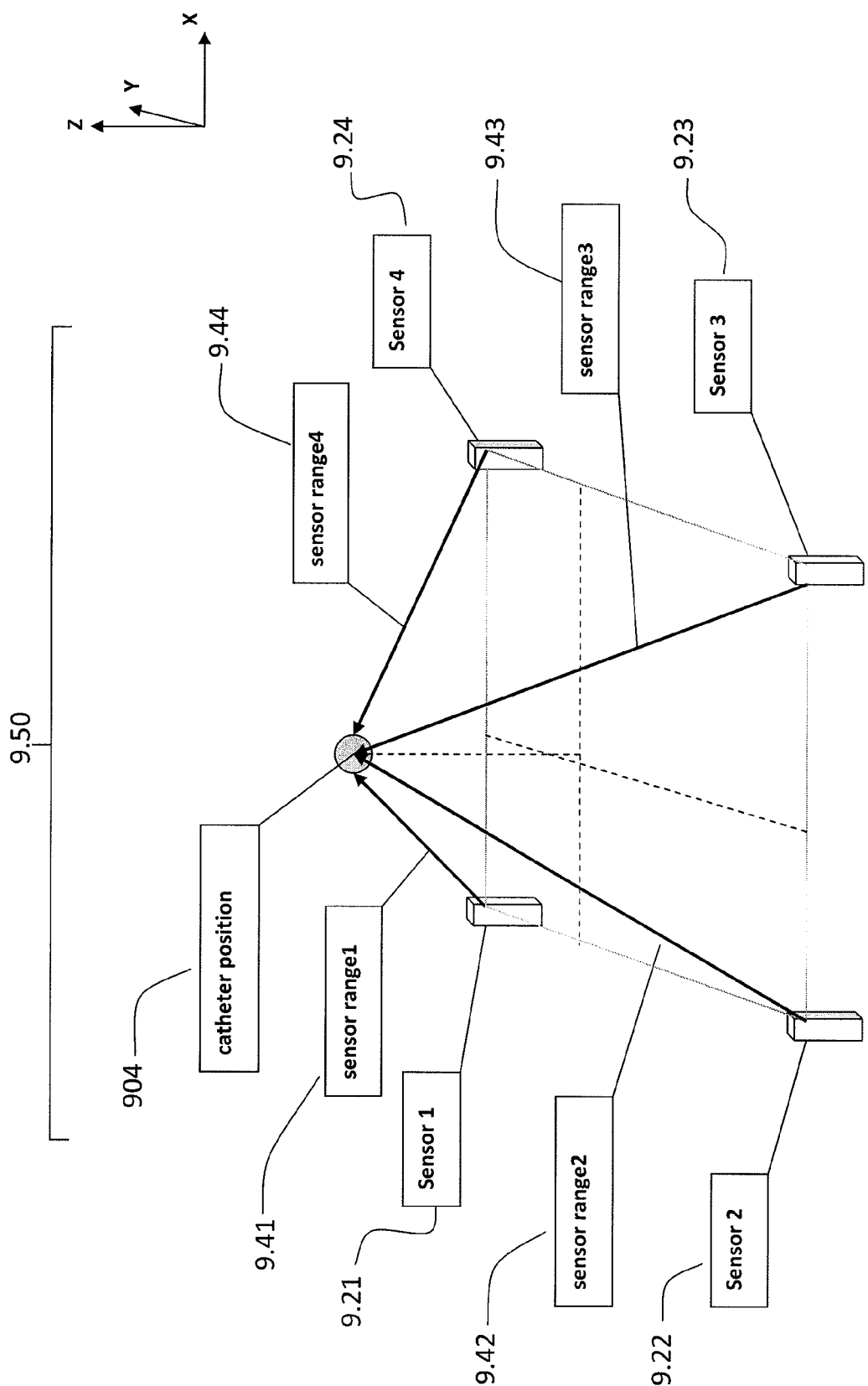
FIG. 9C is a schematic diagram of a catheter position triangulation using four Hall-Effect sensors and their respective range values.

FIG. 9C is a schematic diagram of a catheter position triangulation 9.50 using four Hall-Effect sensors and their respective range values. The magnitude of the magnetic field at each sensor 9.1-9.4 is converted to a range value Sensor-Range1-SensorRange4 9.41-9.44 by a magnetic field to distance calibration curve, the sensor ranging dataset 9.40 (not shown). The positions of magnetic sensor 1-4 9.11-9.14 are known and fixed values and form the baseline for triangulating the catheter position 904 (which is the positional component of the Actual Position, AP 20), which is always above the detection sensor array.

Figure 9D:
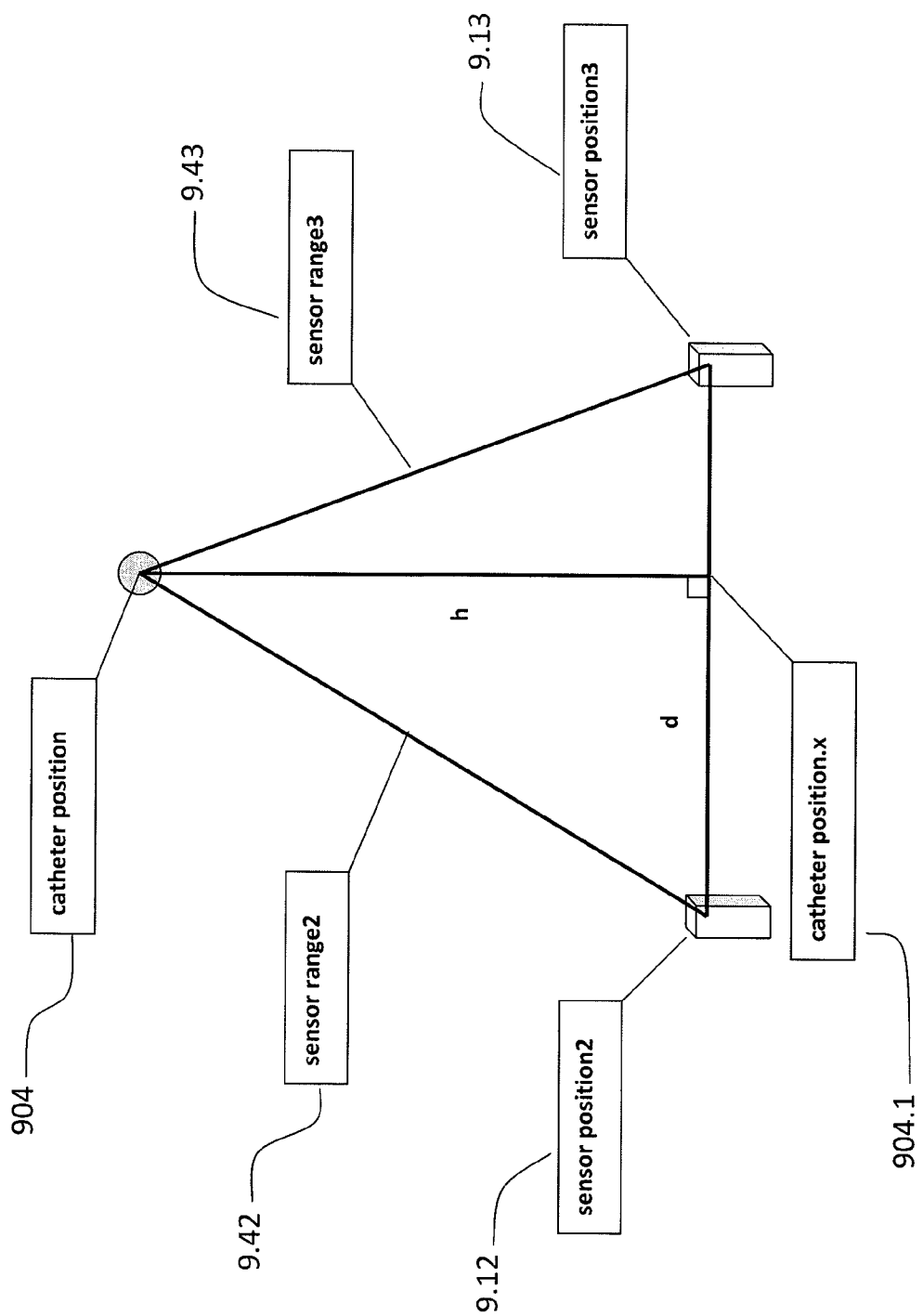
FIG. 9D is a detailed schematic of the triangulation of the catheter position's X-coordinate using two sensors.

FIG. 9D is a detailed schematic of the triangulation of the catheter position's X-coordinate using two sensors, sensor #2 9.22 and sensor #3 9.23. Using standard Trigonometry, SensorRange2 9.42 and SensorRange3 9.43 are used with SensorPosition2 9.12 and SensorPosition3 9.13 to locate the x-coordinate of the catheter position 904, CatheterPositionX 904.1. In similar calculations, two solutions for CatheterPositionX 904.1 and CatheterPositionY 904.2 are calculated and averaged. CatheterPositionZ 904.3 is then determined as the average Trigonometric solution for each SensorRange value 9.41-9.44 and CatheterPositionX 904.1 and CatheterPositionY 904.2, giving the three Cartesian components to the catheter position 904.

Figure 9E:
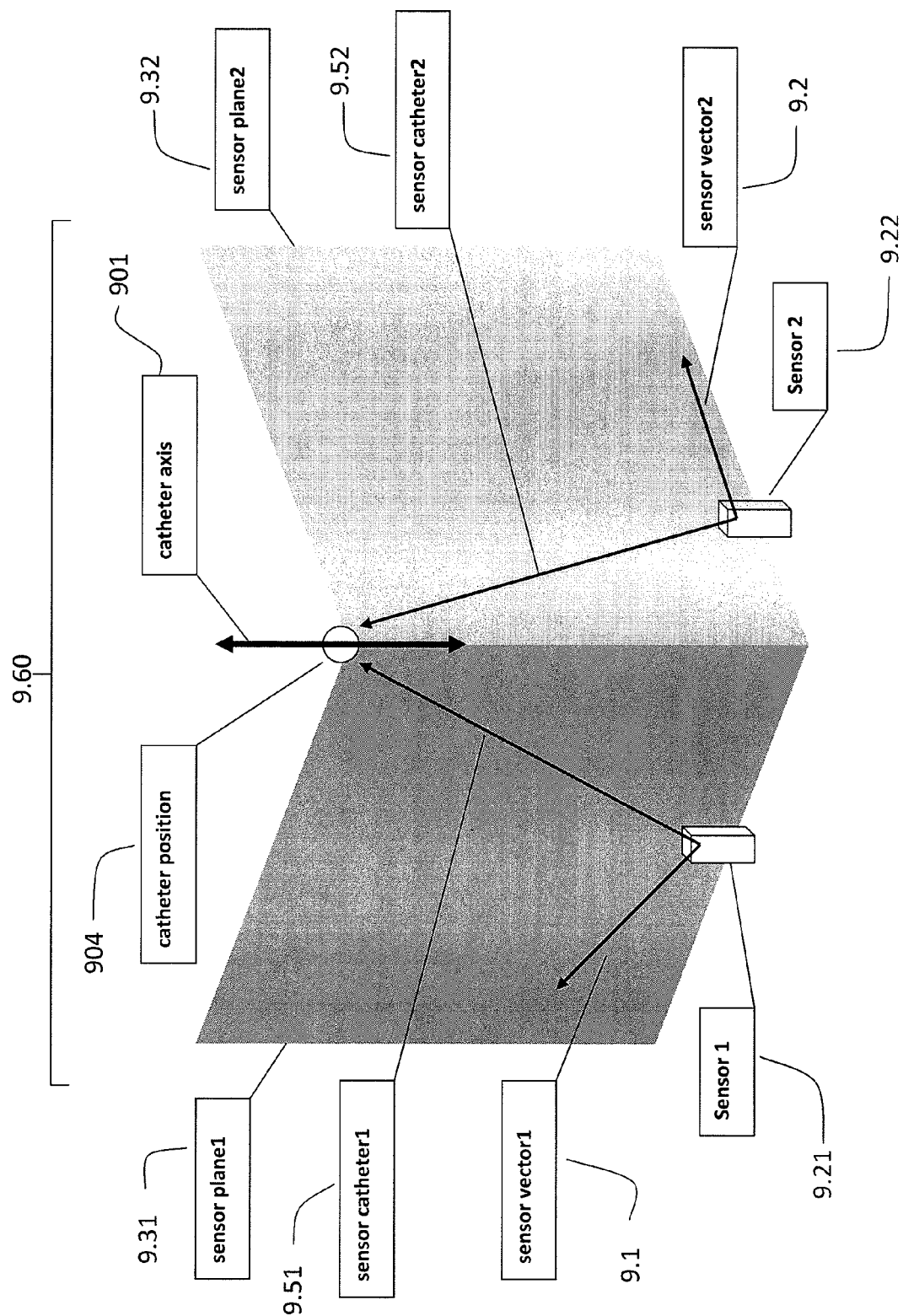
FIG. 9E is a diagram of the Intersecting Planes Method for determining the orientation of a magnetic catheter tip from its position and two sensor's magnetic field values.

FIG. 9E is a diagram of the Intersecting Planes Method 9.60 for determining the orientation of a magnetic catheter tip from its position and two sensor's magnetic field values. When the position of the catheter tip 904 is known, the orientation of the catheter tip's magnetic field axis 901 is calculated as being co-planar with each of the magnetic sensor vectors 9.1-9.4 and their corresponding sensor-to-catheter position vectors, SensorCatheter1-SensorCatheter4 9.51-9.54. The sensor-catheter planes, defined by the plane normal vectors 9.31-9.34, are calculated as the normalized cross-product of the normalized magnetic sensor vectors 9.1-9.4 and normalized sensor-to-catheter vectors 9.51-9.55. The intersection of any two sensor-catheter planes, calculated as the normalized cross-product of the plane normal vectors 9.31-9.34, gives a solution to the catheter magnetic axis 901. The direction of the magnetic axis along the intersection of the planes is determined by examining the direction of the plane normal vectors 9.31-9.34.

Figure 9F:
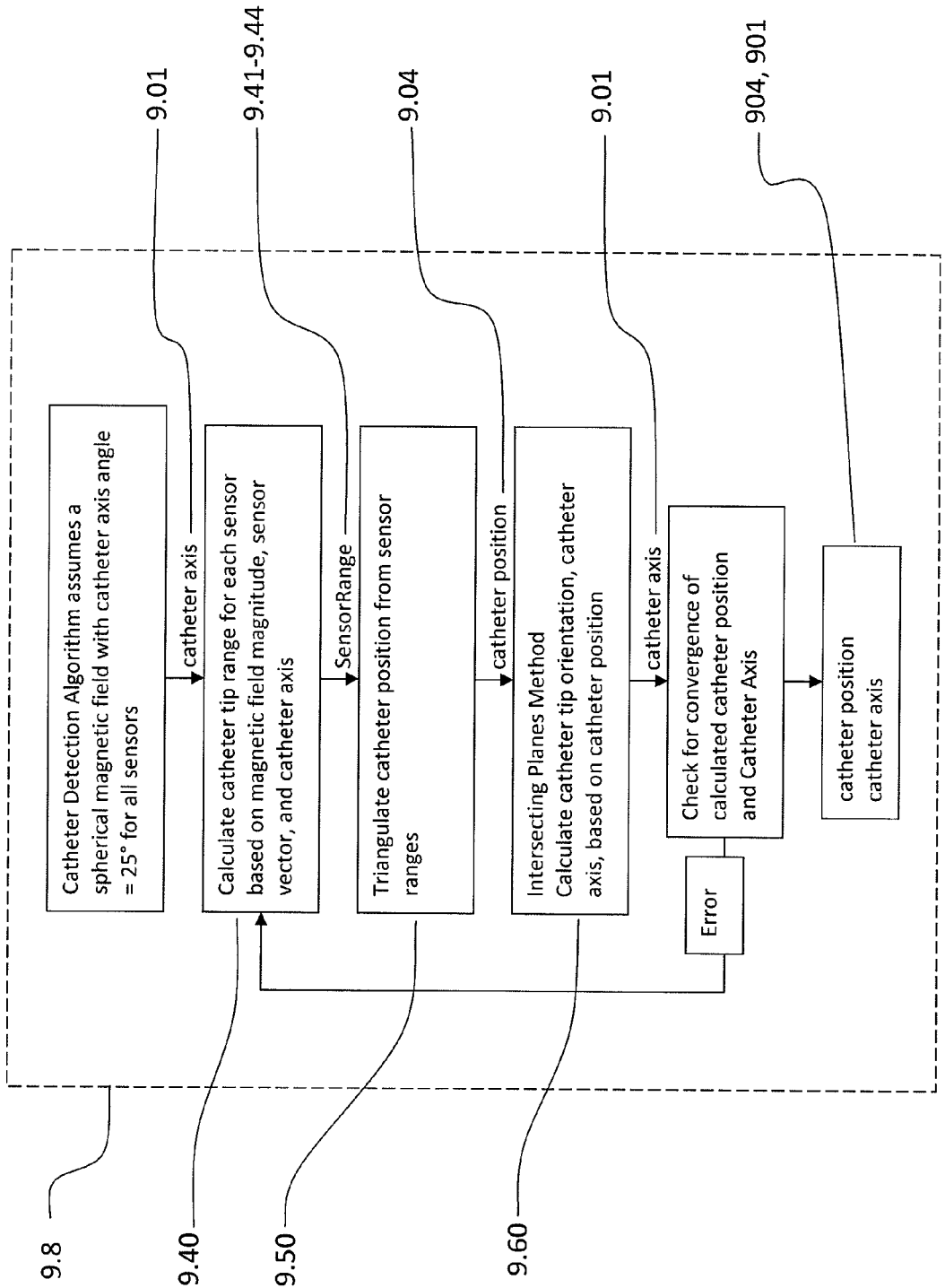
FIG. 9F is a block diagram of the method for determining both position and orientation when they are not independent values.

FIG. 9F is a block diagram of the method for determining both position and orientation when they are not independent values. The Catheter Tip Position and Orientation Calculation Algorithm 9.8 uses an iterative method to determine catheter position 904 and catheter orientation 901 since the catheter tip magnetic field is not spherical so therefore position and orientation are not independent variables. The data for magnetic tip field magnitude versus distance and orientation to the magnetic axis is known and stored internally to the algorithm as a calibrated dataset, the sensor ranging dataset 9.40. The magnetic sensor vectors 9.1-9.4 are first used to calculate the range from each sensor to the magnetic tip using the sensor ranging dataset 9.40, initially using the assumption that the field is spherical with the field magnitude profile equal to a 25-degree declination from the catheter magnetic axis 901. The catheter tip position 904 is then calculated by triangulation 9.50. The catheter position 904 is then used to calculate the catheter's magnetic axis 901 using the Intersecting Planes Method 9.60. The catheter magnetic axis 901 is used to recalculate the SensorRange values from the sensor range dataset 9.40, and then to re-triangulate 9.50 the catheter position 904. The catheter axis is then re-calculated as well by the Intersecting Planes Method 9.60. The iterative method has been determined to be convergent, and when the successive values are within the desired error limits, the catheter position 904 and orientation 901 are known.

Figure 10A:
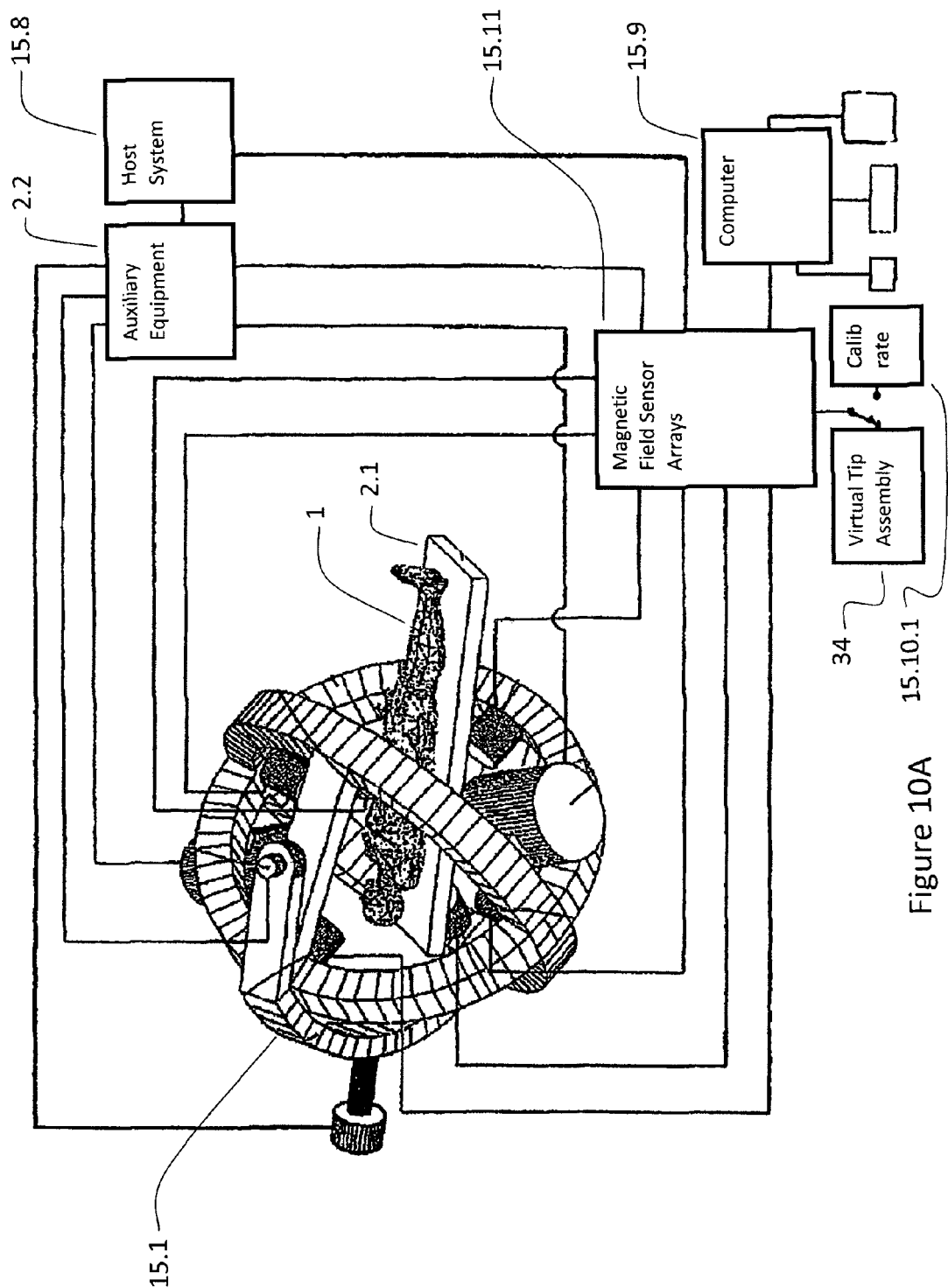
FIG. 10A is a diagram of the signals and systems used in catheter position control.

FIG. 10A is a diagram of the signals and systems used in catheter position control. The Catheter Guidance Control and Imaging System (CGCI) 15 uses the Catheter Position Detection System (CPDS) 7 information and a magnetic chamber 15.1 to push, pull, and steer a magnetically-tipped catheter 3 within the patient 1. The operator uses the Virtual Tip 34 controller to specify a desired catheter position and orientation, DP 30, in the CGCI, and the CGCI uses the actual position and orientation of the catheter, AP 20, which is received from the CPDS to control the catheter in a closed-loop regulation mode. The CGCI "Host System" Controller computer 15.8 performs the real-time regulation of the CGCI using information from the CGCI Magnetic Field Sensor Arrays 15.11, Virtual Tip 34, and additional medical signals from the Auxiliary Equipment 2.2. The Console computer 15.9 serves as the operator interface with a monitor, mouse and keyboard next to the Virtual Tip 34. The Virtual Tip 34 is calibrated with an additional calibration fixture 15.10.1 before the operation begins.

Figure 10B:
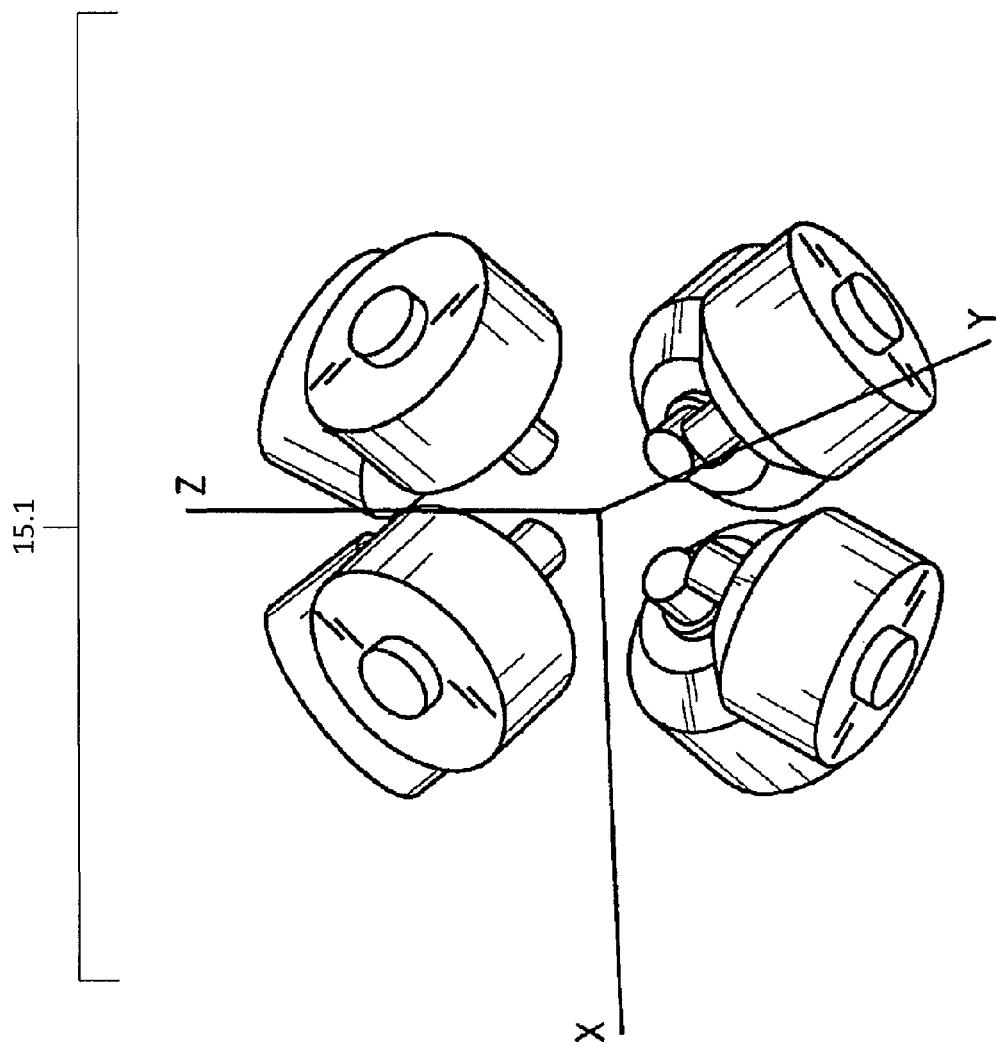
FIG. 10B is an isometric diagram of another embodiment of the magnetic chamber used to control catheter position.

FIG. 10B is an isometric diagram of another embodiment of the magnetic chamber used to control catheter position. In this embodiment, the magnetic chamber 15.1 is included of eight electromagnetic coils which is an optimized design to generate a magnetic guidance lobe while providing sufficient patient access.

Figure 10C:
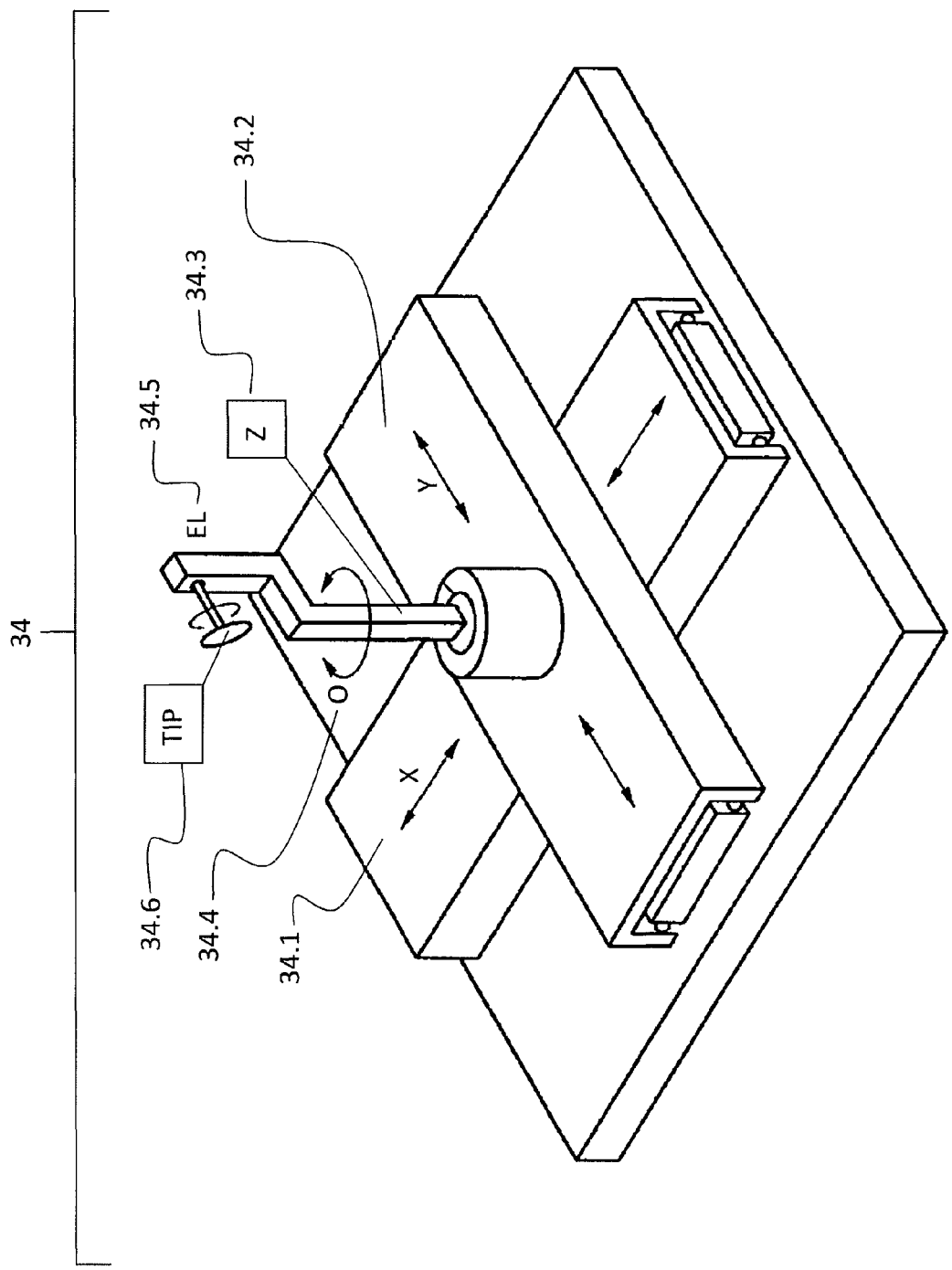
FIG. 10C is an isometric diagram of a virtual tip assembly.

FIG. 10C is an isometric diagram of the Virtual Tip assembly 34. The control end of the Virtual Tip can be moved in six-degrees of freedom, including the X 34.1, Y 34.2, Z 34.3 Cartesian directions, Rotated 34.4, Elevated 34.5, and Twisted 34.6.

Figure 11A:
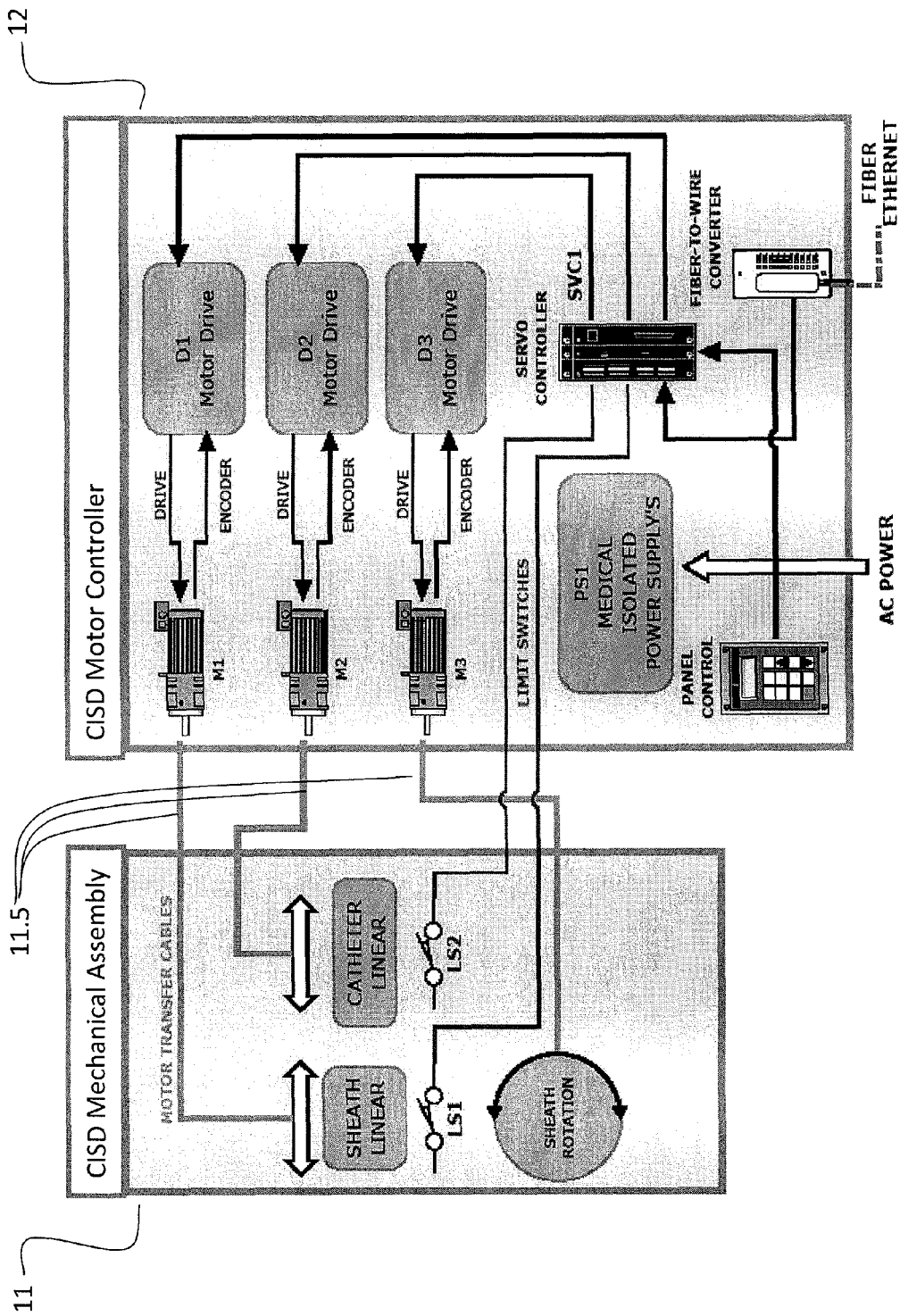
FIG. 11A is a block diagram of the signals and systems of the CISD Mechanical Assembly and CISD Motor Controller.

FIG. 11A is a block diagram of the signals and systems of the CISD Mechanical Assembly and CISD Motor Controller. The CISD Motor Controller 12 (for the purposes of this patent is considered an external, off-the-shelf device) controls the position of the CISD Mechanical Assembly 11 (see FIGS. 11B-11E) components through the CISD Drive Cables 11.5. The CISD Motor Controller 12 includes a set of three off-the-shelf packaged stepper motors, encoders, limit switches and stepper motor controllers. Each motor assembly actuates one of the three CISD Drive Cables 11.5, two of which are linear drive cables, and one is a rotational drive cable. The motor controller assemblies accept a standard positional signal over the local Ethernet bus.

Figure 11B:
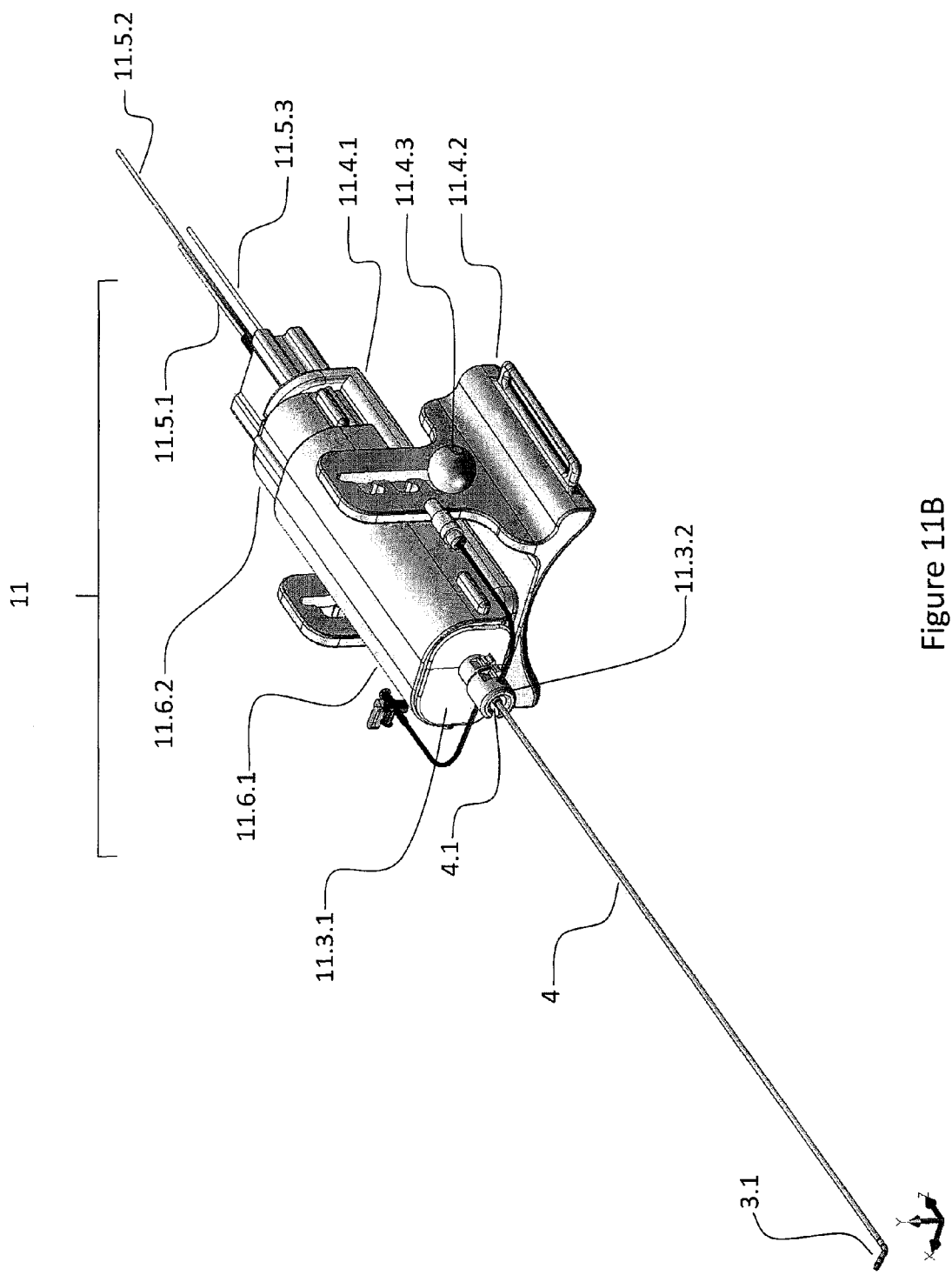
FIG. 11B is an isometric drawing of an embodiment of the CISD Mechanical Assembly.

FIG. 11B is an isometric drawing of an embodiment of the CISD Mechanical Assembly 11. In this embodiment, the CISD Motor Controller 11.1 (not shown) controls the device through the CISD Drive Cables (11.5.1, 11.5.2, 11.5.3). The CISD Mechanical Assembly 11 contains no motors or electronics, and may be sterilized so that it is compatible with a surgical environment. The CISD Base Plate 11.4.1 is attached to the CISD Leg Mount 11.4.2 by the CISD Mount Pin 11.4.3 which allows the operator to elevate and rotate the CISD Mechanical Assembly 11, as to align the device within the surgical environment. The drive elements are housed under protective telescoping covers. The CISD Outer Cover 11.6.1 is attached to the Sheath Rotator Housing 11.3.1 on the Sheath Shuttle 11.3 (see FIG. 4), and the CISD Inner Cover 11.6.2 is attached to the CISD Base Plate 11.4.1. As the Sheath Shuttle 11.3 moves forward and backward along the CISD Base Plate 11.4.1, the CISD Covers 11.61, 11.62 telescope over each other. The Sheath Shuttle 11.3 pushes the sheath back and forth with respect to the patient's leg. The Sheath Rotator Housing 11.3.1 is mounted on the end of the Sheath Shuttle 11.3 and contains gears that rotate the Sheath Rotator Clip 11.3.2. The proximal end of the Sheath 4 has the standard Hemostatic Seal 4.1 which is held within the Sheath Rotator Clip 11.3.2. The Catheter Tip 3.1 is inserted through the rear of the CISD Mechanical Assembly 11 and through the attached Sheath 4.

Figure 11C:
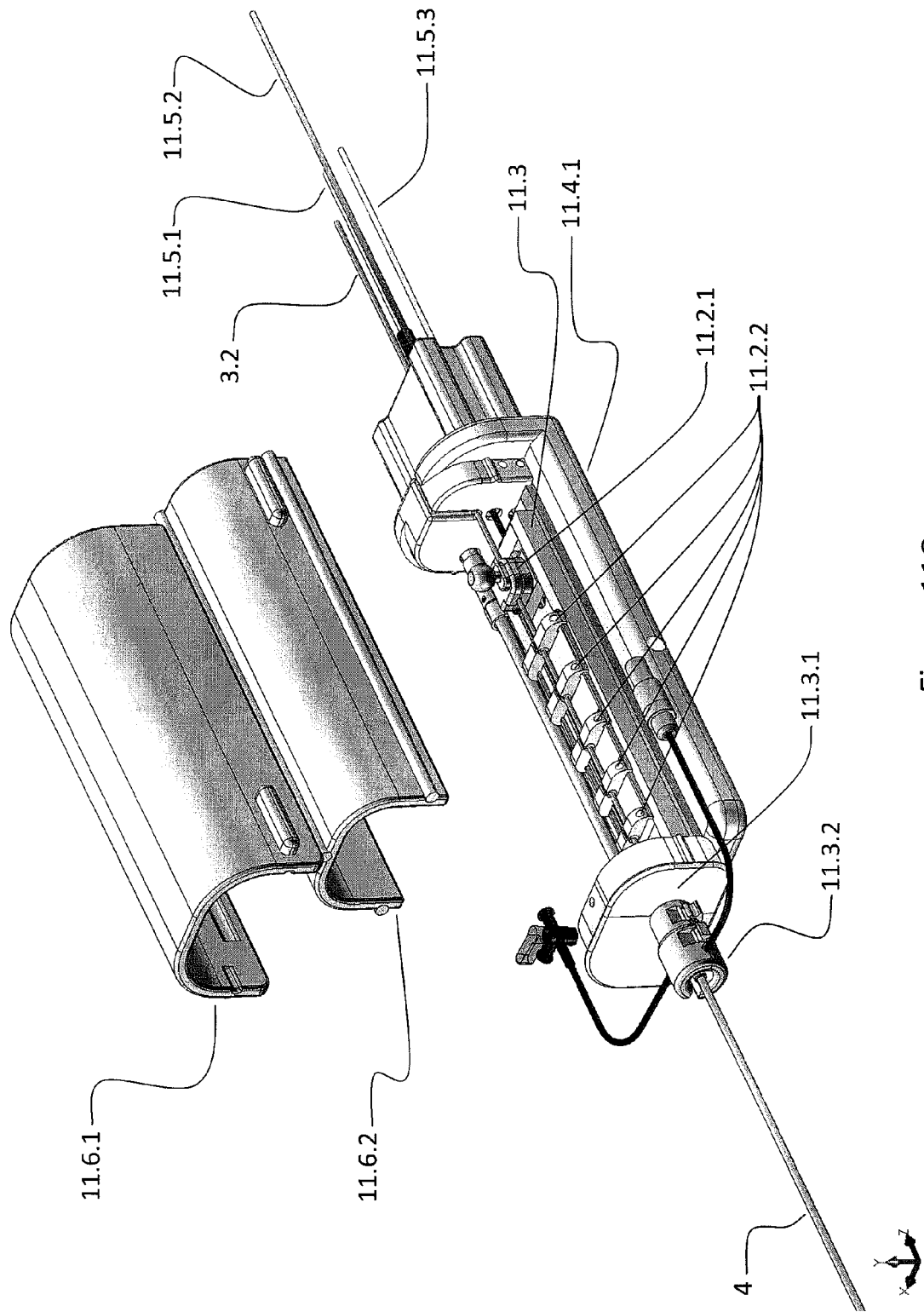
FIG. 11C is an isometric detail drawing of the internal assemblies within the CISD Mechanical Assembly.

FIG. 11C is an isometric detail drawing of the internal assemblies within the CISD Mechanical Assembly. The CISD Covers 11.6.1, 11.6.2 and CISD Leg Mount have been removed for clarity. The Sheath Shuttle 11.3 is moved over the CISD Base Plate 11.4.1 by the Sheath Shuttle Cable 11.5.3. On the Sheath Shuttle 11.3, the Catheter Shuttle Clamp 11.2.1 is attached to the Catheter Shuttle 11.2 and clamps to the Catheter Shaft 3.2. The Catheter Shuttle 11.2 is moved by the Catheter Shuttle Cable 11.5.2 which moves the Catheter 3 with reference to the Sheath 4. The spacing of the Catheter Alignment Supports 11.2.2 changes with the movement of the Catheter Shuttle 11.2 to keep the catheter line from kinking as it is pushed. The Sheath Rotator Cable 11.5.1 rotates the gears within the Sheath Rotator Housing 11.3.1 (see FIG. 6), which rotates the Sheath Rotator Clip 11.3.2 to which is fitted the Sheath Hemostatic Seal 4.1, allowing for the rotation of the Sheath 4.

Figure 11D:
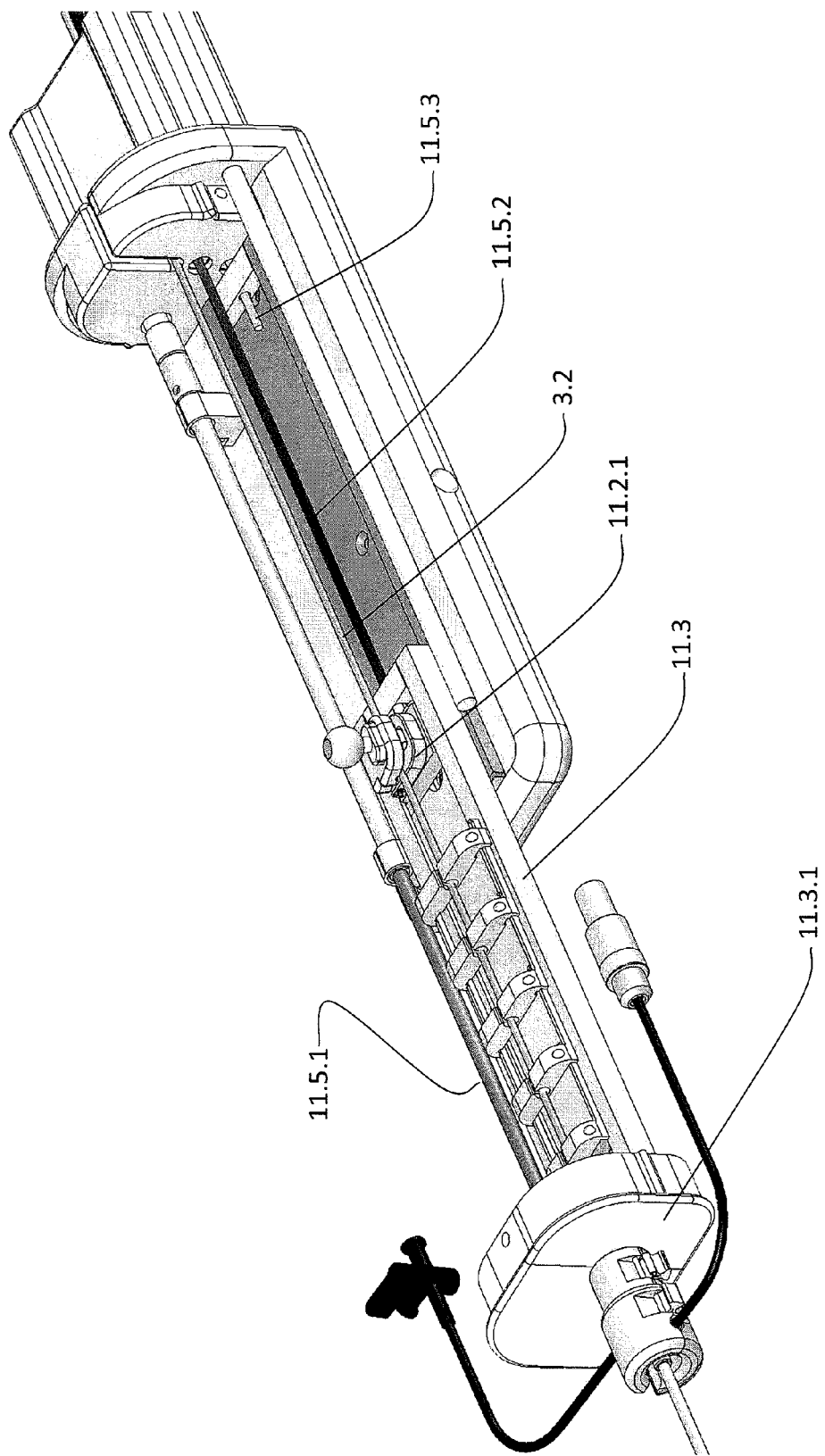
FIG. 11D is an isometric drawing showing the sheath shuttle in a forward position.

FIG. 11D is an isometric drawing showing the Sheath Shuttle in a forward position. The Sheath Shuttle 11.3 is moved by the Sheath Shuttle Cable 11.5.3. The Catheter Shuttle Cable 11.5.2 is attached to the Catheter Shuttle Clamp 11.2.1 to move the Catheter Line 3.2 with reference to the Sheath 4. The end of the Sheath Rotator Cable 11.5.1 telescopes with the Sheath Shuttle 11.3, and drives the gears within the Sheath Rotator Housing 11.3.1.

Figure 11E:
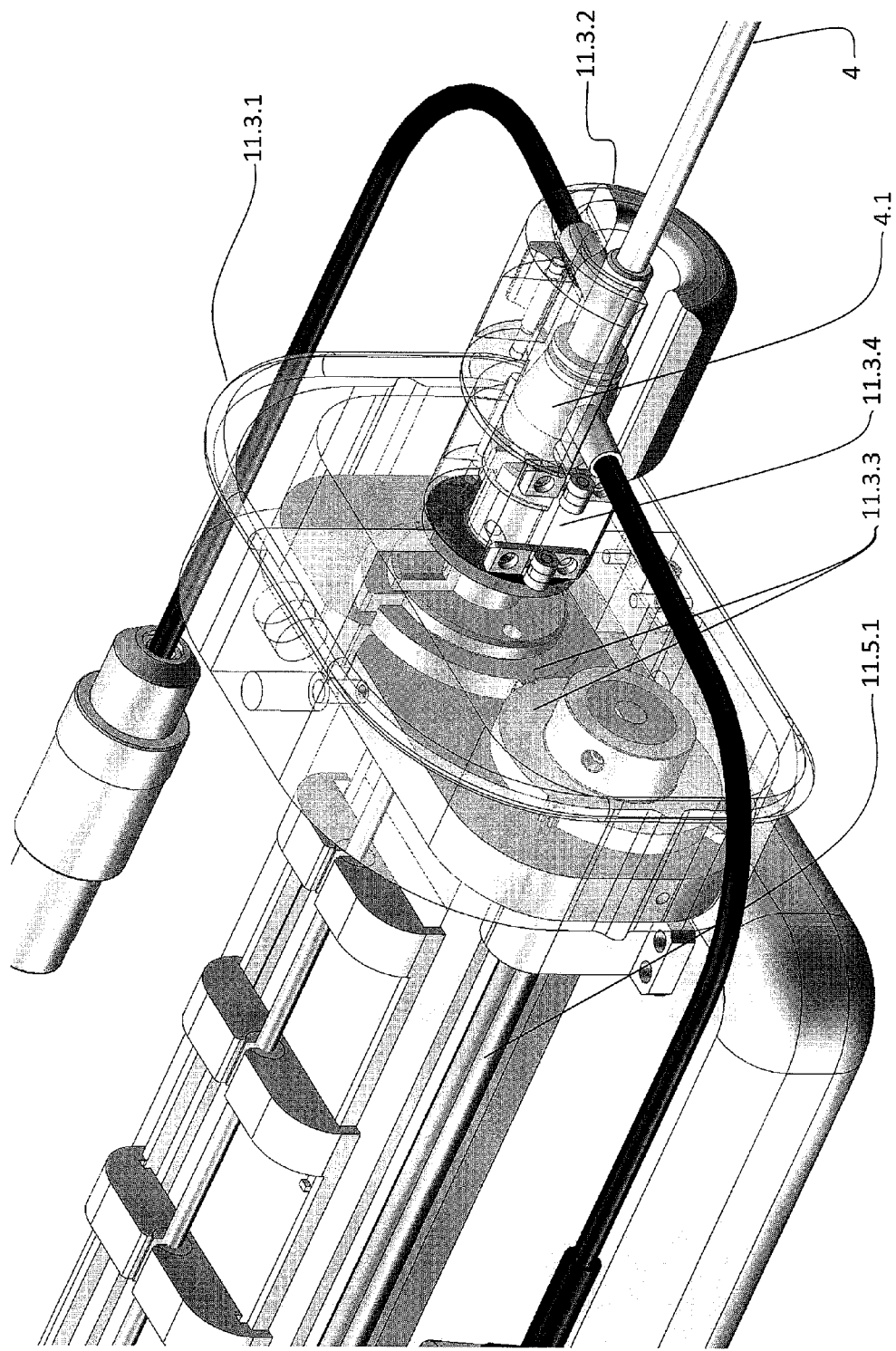
FIG. 11E is an isometric detail drawing of the sheath rotator housing.

FIG. 11E is an isometric detail drawing of the sheath rotator housing. Inside the Sheath Rotator Housing 11.3.1, the Sheath Rotator Cable 11.5.1 turns the Sheath Rotator Drive Gears 11.3.3 to turn the Sheath Rotator Clip 11.3.2. The Sheath's Hemostatic Seal 4.1 clips within the Sheath Rotator Clip 11.3.2. The Sheath Rotator Torque Limiting Assembly 11.3.4 limits the amount of torque that may be applied to the sheath, as to keep the mechanical stress within safe limits.

It will be evident to those skilled in the art that the invention is not limited to the details of the foregoing illustrated embodiments and that the present invention may be embodied in other specific forms without departing from the spirit or essential attributed thereof; furthermore, various omissions, substitutions and changes may be made without departing from the spirit of the inventions. The foregoing description of the embodiments is therefore to be considered in all respects as illustrative and not restrictive, with the scope of the invention being delineated by the appended claims and their equivalents.

What is claimed is:

1. An apparatus for making and maintaining continuous tissue contact between a tool tip and moving tissue in a patient, comprising:
   a controllable magnetic field source that produces a magnetic field;
   a tool having a distal end responsive to said magnetic field;
   one or more sensors configured to sense a current vector position of said distal end by measuring one or more impedances;
   a controller for controlling said magnetic field source to control a movement of said distal end according to a feedback calculation wherein said system controller is configured to compute a position error comprising a difference between a desired vector position of said distal end and said current vector position of said distal end; and
   an operator control that provides tactile feedback to an operator when said position error exceeds a predetermined amount, wherein said tactile feedback is computed by said controller at least in part according to said vector position error, wherein a correction input to said desired vector position is computed based on a position of a heart relative to a frame of reference, such that said system controller compensates for a dynamic position of a wall of a heart chamber such that said distal end maintains contact with said wall of said heart chamber at least in part by measuring at least one impedance between said distal end and said wall.

2. The apparatus of claim 1, wherein said tool comprises a Lorenz sheath.

3. The apparatus of claim 1, further comprising one or more patches provided to said patient, wherein said apparatus measures a position and orientation of a Lorenz sheath at least in part by measuring one or more impedances between said Lorenz sheath and said conductive patches.

4. The apparatus of claim 1, wherein said controller is configured to control said magnetic field source to maintain said distal end in a desired vector orientation relative to said wall.

5. The apparatus of claim 1, wherein said controller is configured to control said magnetic field source to maintain said distal end substantially normal to said wall.

6. The apparatus of claim 1, wherein said controller is configured to differentiate between contact with said wall and contact with an obstruction by analyzing differences between a measured impedance and an expected impedance.

7. The apparatus of claim 6, wherein said controller is configured to compute a path around said obstruction.

8. The apparatus of claim 1, wherein said controller is configured to control said magnetic field source to maintain said distal end in a desired orientation relative to said wall.

9. The apparatus of claim 1, wherein said controller is configured to differentiate between contact with said wall and contact with other tissue by analyzing differences between a measured impedance and an expected impedance, said expected impedance corresponding to said wall.

10. The apparatus of claim 1, wherein said other tissue comprises a blood pool.

11. The apparatus of claim 1, wherein said controller is configured to seek contact with said wall by calculating a target manifold, monitoring a distal end-to-target vector with respect to said target manifold, calculating a new tool length, and adjusting a length of said tool according to said new tool length.

12. The apparatus of claim 1, wherein said tool comprises an introducer.

13. The apparatus of claim 12, wherein said controller controls a rotation and translation of said introducer.

14. A method for positioning a surgical tool and maintaining relatively continuous contact between a distal end of said tool and a desired tissue location, comprising:
controlling a position and orientation of a distal end of a surgical tool by adjusting currents in a plurality of electromagnets;
measuring a plurality of impedance values between said distal end and a plurality of tissue locations;
constructing an impedance map at least in part form said plurality of impedance values;
determining a first impedance value corresponding to an impedance measured when said distal end touches said desired tissue location; and
using a feedback controller to control said currents to maintain contact between said distal end and said desired tissue such that said distal end is oriented relatively normal to said desired tissue location in the presence of motion of said desired tissue location, wherein feedback information to said feedback controller comprises periodic impedance measurements between said distal end and said desired tissue location.

15. The method of claim 14, further comprising:
computing a position error comprising a difference between a desired vector position of said distal end and said current vector position of said distal end; and
providing tactile feedback to an operator control when said position error exceeds a predetermined amount, wherein said tactile feedback is computed at least in part according to said position error.

16. The method of claim 14, wherein said tool comprises a Lorenz sheath.

17. The method of claim 14, further comprising locating said distal end by measuring impedances between a plurality of patches provided to said patient and said surgical tool.

18. The method of claim 14, further comprising differentiating between contact with said desired tissue location and contact with an obstruction by analyzing differences between a measured impedance and an expected impedance.

19. The method of claim 15, further comprising computing a path around said obstruction.

20. The method of claim 14, further comprising distinguishing between contact with said desired tissue location and contact with other tissue by analyzing differences between a measured impedance and an expected impedance, said expected impedance corresponding to an impedance at said desired tissue location.

21. The method of claim 20, wherein said other tissue comprises a blood pool.

22. The method of claim 14, further comprising seeking contact with said desired tissue location by:
calculating a target manifold;
monitoring a distal end-to-target vector with respect to said target manifold;
calculating a new tool length; and
adjusting a length of said tool according to said new tool length.

23. The method of claim 14, wherein said tool comprises an introducer.

24. The method of claim 14, further comprising controlling a rotation and translation of said tool.

* * * * *